(12) United States Patent
Eberle et al.

(10) Patent No.: US 10,717,982 B2
(45) Date of Patent: Jul. 21, 2020

(54) STABILIZATION OF POLY(A) SEQUENCE ENCODING DNA SEQUENCES

(71) Applicants: BioNTech RNA Pharmaceuticals GmbH, Mainz (DE); TRON—Translationale Onkologie an der Universitätsmedizin der Johannes Gutenberg-Universität Mainz gGmbH, Mainz (DE)

(72) Inventors: Florian Eberle, Dossenheim (DE); Ugur Sahin, Mainz (DE); Andreas Kuhn, Mainz (DE); Britta Vallazza, Hagen (DE); Mustafa Diken, Mainz (DE)

(73) Assignees: BioNTech RNA Pharmaceuticals GmbH, Mainz (DE); TRON—Translationale Onkologie an der Universitätsmedizin der Johannes Gutenberg-Universität Mainz gGmbH, Mainz (DE)

( * ) Notice: Subject to any disclaimer, the term of this patent is extended or adjusted under 35 U.S.C. 154(b) by 82 days.

(21) Appl. No.: 15/325,280

(22) PCT Filed: Jul. 6, 2015

(86) PCT No.: PCT/EP2015/065357
§ 371 (c)(1),
(2) Date: Jan. 10, 2017

(87) PCT Pub. No.: WO2016/005324
PCT Pub. Date: Jan. 14, 2016

(65) Prior Publication Data
US 2017/0166905 A1   Jun. 15, 2017

(30) Foreign Application Priority Data

Jul. 11, 2014   (WO) ................ PCT/EP2014/064924

(51) Int. Cl.
| | | |
|---|---|---|
| *C12N 15/68* | (2006.01) | |
| *C12N 15/70* | (2006.01) | |
| *C12N 15/67* | (2006.01) | |
| *A61K 39/00* | (2006.01) | |
| *A61K 48/00* | (2006.01) | |
| *C12N 15/85* | (2006.01) | |
| *C12P 19/34* | (2006.01) | |
| *C12P 21/00* | (2006.01) | |

(52) U.S. Cl.
CPC .............. *C12N 15/68* (2013.01); *A61K 39/00* (2013.01); *A61K 48/0066* (2013.01); *C12N 15/67* (2013.01); *C12N 15/70* (2013.01); *C12N 15/85* (2013.01); *C12P 19/34* (2013.01); *C12P 21/00* (2013.01); *A61K 2039/53* (2013.01); *C12N 2830/50* (2013.01)

(58) Field of Classification Search
None
See application file for complete search history.

(56) References Cited

U.S. PATENT DOCUMENTS

| | | | | |
|---|---|---|---|---|
| 5,866,422 A | * | 2/1999 | Wayne ..................... | C12N 9/22 435/193 |
| 2003/0235584 A1 | * | 12/2003 | Kloetzer ............ | A01K 67/0276 424/145.1 |
| 2014/0087444 A1 | * | 3/2014 | Bennett .................. | C12N 15/86 435/235.1 |

FOREIGN PATENT DOCUMENTS

| | | |
|---|---|---|
| AU | 2011253592 A1 | 12/2011 |
| WO | 2007036366 A8 | 5/2012 |

OTHER PUBLICATIONS

Holtkamp et al., Modification of antigen-encoding RNA increases stability, translational efficacy, and T-cell stimulatory capacity of dendritic cells, Blood, Dec. 15, 2006, vol. 108, No. 13.*
Bernstein et al., The Poly(A)-Poly(A)-Binding Protein Complex is a Major Determinant of mRNA Stability In Vitro, Molecular and Cellular Biology, Feb. 1989, p. 659-670.*
Jain, Degradation of mRNA in *Escherichia coli*, IUBMB Life, 54: 315-321, 2002.*
Bergman et al., Transformation in *Escherichia coli*: Stages in the Process , Journal of Bacteriology, May 1981, p. 564-570.*
Angelichio et al., Comparison of several promoters and polyadenylation signals for use in heterologous gene expression in cultured Drosophila cells, Nucleic Acids Research, vol. 19, No. 18 5037-5043.*
Wu et al., Secondary Structure as a Functional Feature in the Downstream Region of Mammalian Polyadenylation Signals, Molecular and Cellular Biology, Apr. 2004, p. 2789-2796.*
Carswell et al., Efficiency of Utilization of the Simian Virus 40 Late Polyadenylation Site: Effects of Upstream Sequences, Molecular and Cellular Biology, Oct. 1989, p. 4248-4258.*
Ribeiro et al in "The role of polyadenylation signal secondary structures on the resistance of plasmid vectors to nucleases" (J Gene Med. May 2004, vol. 6, No. 5, pp. 565-573) (Year: 2004).*

(Continued)

*Primary Examiner* — Catherine S Hibbert
(74) *Attorney, Agent, or Firm* — Choate, Hall & Stewart LLP; Brenda Herschbach Jarrell; Janet M. Tse

(57) ABSTRACT

The present invention relates to nucleic acid molecules containing poly (dA:dT) regions which are stabilized in *E. coli*, methods of propagating such nucleic acid molecules in *E. coli*, methods of obtaining RNA, peptides or proteins using such nucleic acid molecules and to RNA which is obtained from such nucleic acid molecules and its use. In particular, the poly (dA:dT) regions contain at least one disruption by a sequence not encoding a sequence solely composed of A residues.

Figure 1A:
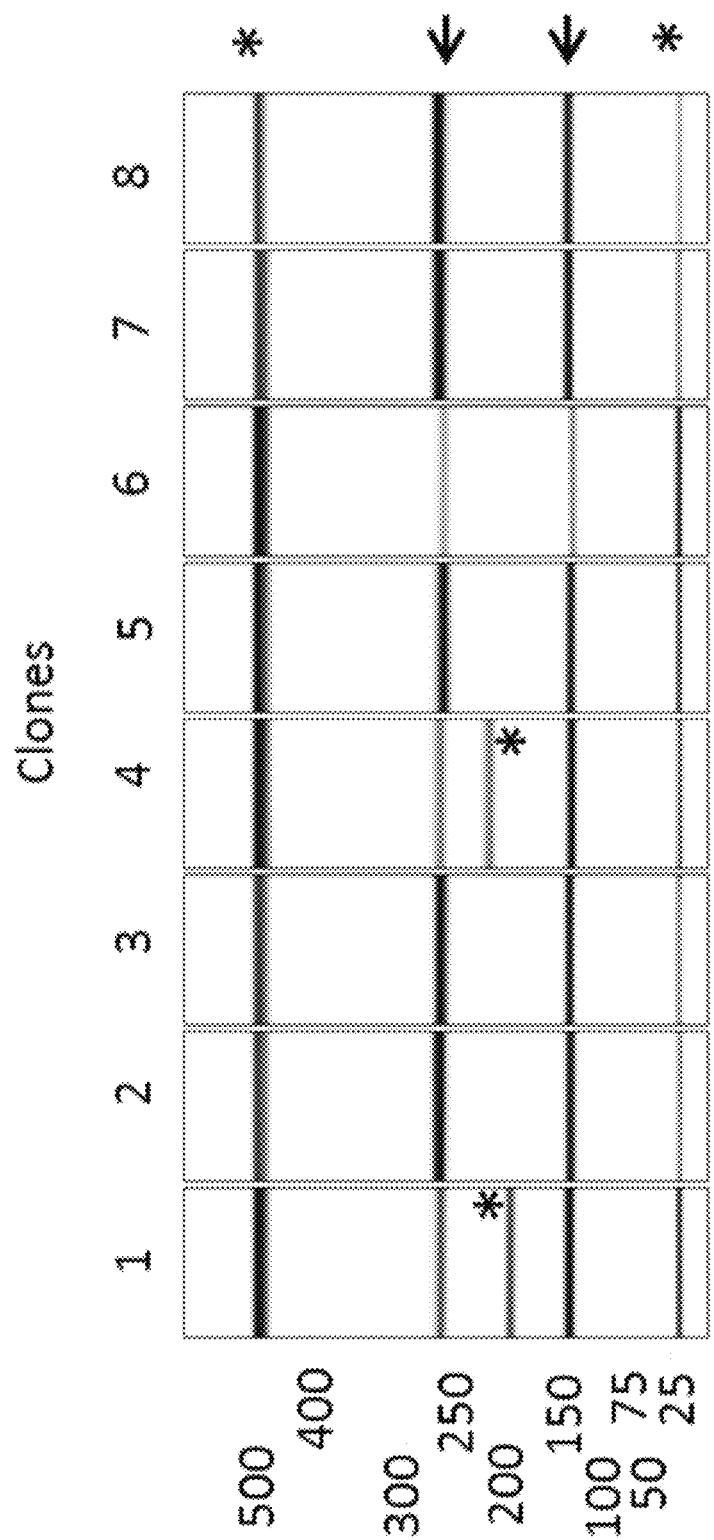

19 Claims, 10 Drawing Sheets
Specification includes a Sequence Listing.

(56) References Cited

OTHER PUBLICATIONS

Azzoni et al in "The impact of polyadenylation signals on plasmid nucleases-resistance and transgene expression" (J Gene Med. 2007; vol. 9, pp. 392-402). (Year: 2007).*
Holtkamp et al. (2006). "Modification of antigen-encoding RNA increases stability, translational efficacy, and T-cell stimulatory capacity of dendritic cells," Blood. 108(13):4009-17.
Kuhn et al. (2011). "Determinants of intracellular RNA pharmacokinetics: Implications for RNA-based immunotherapeutics," RNA Biol. 8(1):35-43.
May 28, 2019—(JP) Office Action—App 2017-521299—Eng Tran.

* cited by examiner

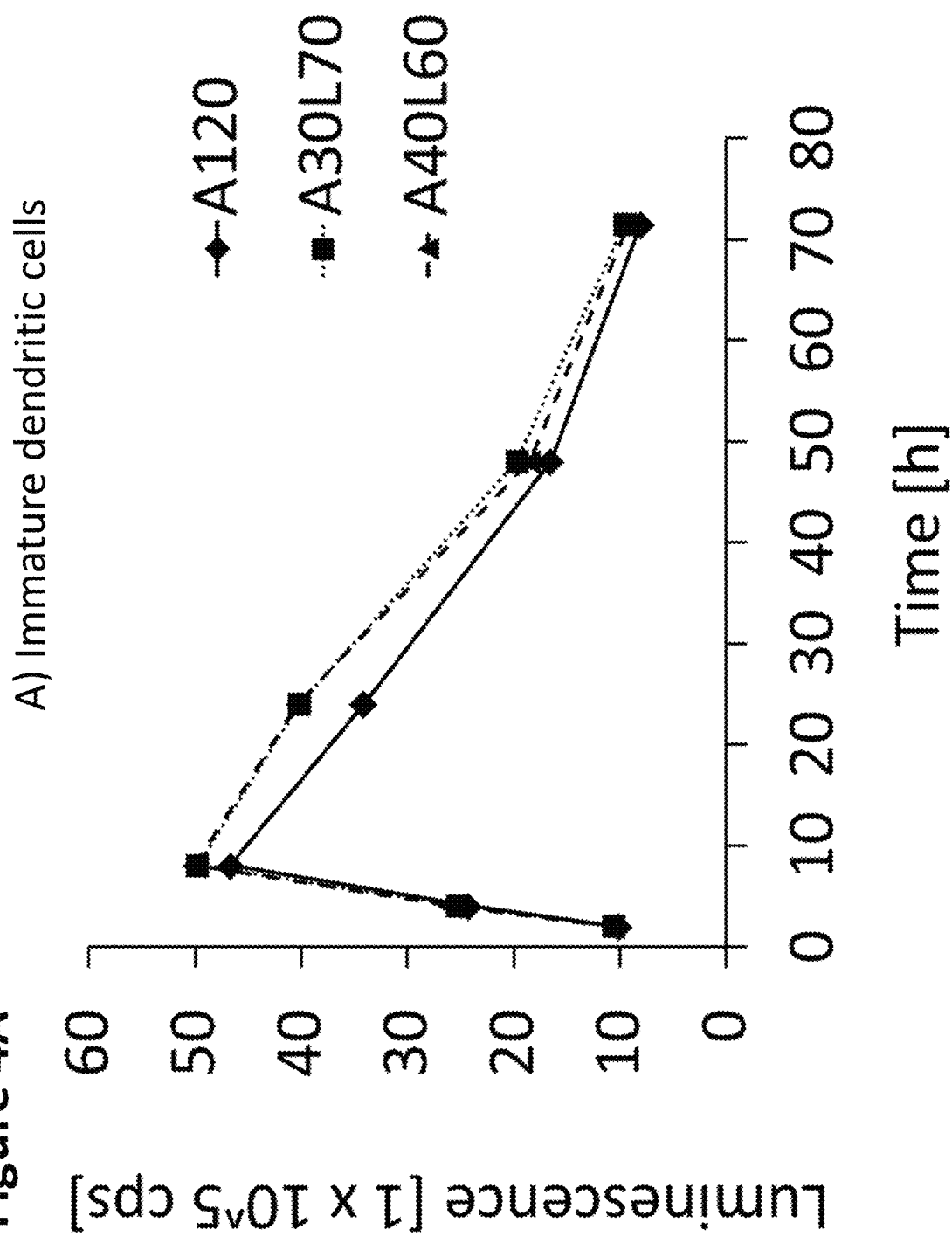

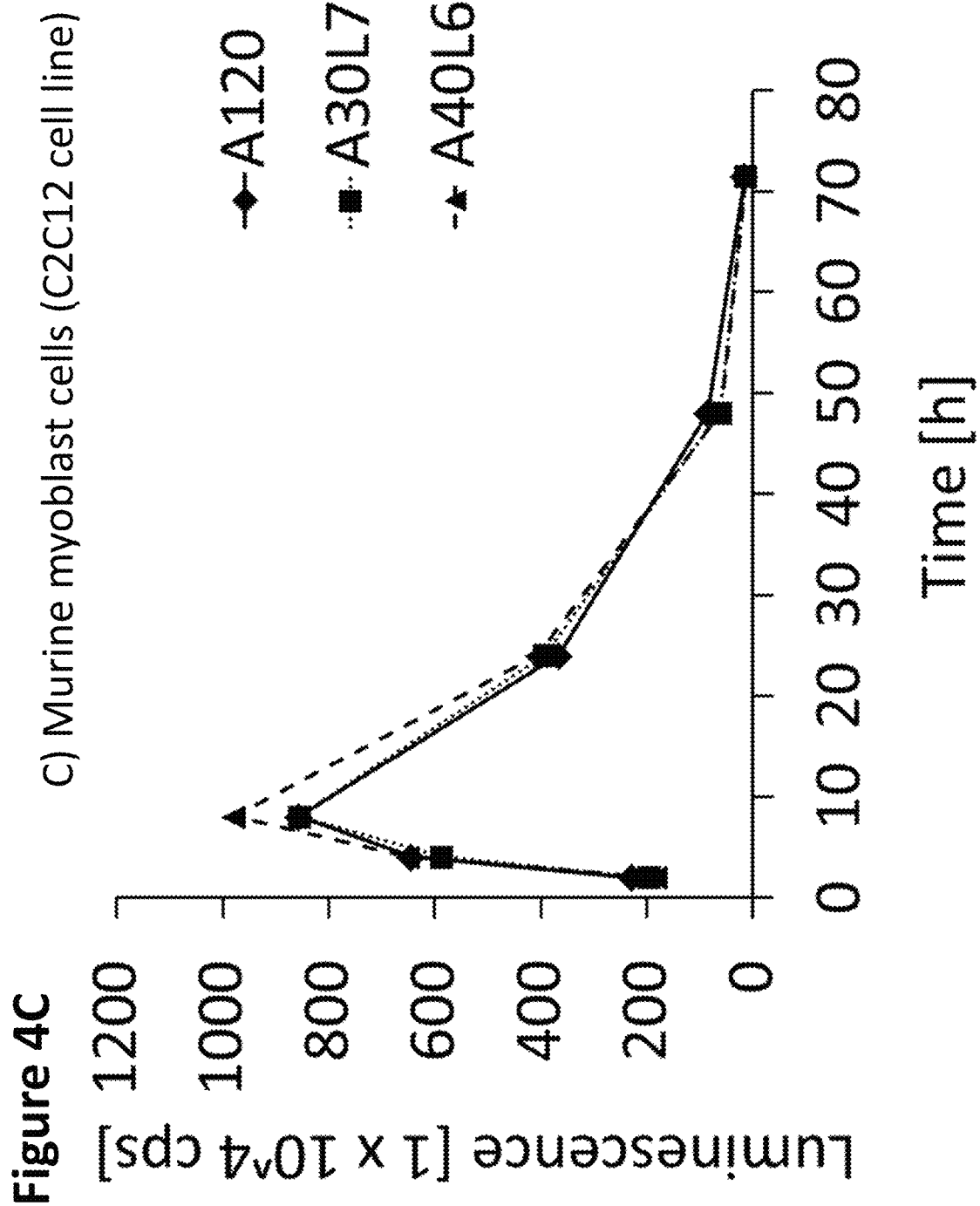

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Ser Ile Ile Asn Phe Glu Lys Leu
1               5

<210> SEQ ID NO 2
<211> LENGTH: 10
<212> TYPE: DNA
<213> ORGANISM: Artificial Sequence
<220> FEATURE:
<223> OTHER INFORMATION: Synthetic Construct

<400> SEQUENCE: 2
gcatatgact                                                              10
```

STABILIZATION OF POLY(A) SEQUENCE ENCODING DNA SEQUENCES

CROSS REFERENCE TO RELATED APPLICATIONS

This application is a U.S. National Phase patent application of PCT/EP2015/065357, filed on Jul. 6, 2015, which claims priority to International Patent Application No. PCT/EP2014/064924, filed on Jul. 11, 2014, the disclosures of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392038600SEQLIST.txt, date recorded: Jan. 4, 2017, size: 1 KB).

BACKGROUND

The use of RNA offers an attractive alternative to DNA in order to circumvent the potential safety risks connected with the therapeutic use of DNA. In vitro-transcribed RNA (IVT-RNA) is of particular interest in therapeutic approaches. The advantages of a therapeutic use of RNA include transient expression and a non-transforming character. RNA does not need to enter the nucleus in order to be expressed and moreover cannot integrate into the host genome, thereby eliminating the risk of oncogenesis. When used for vaccination, injection of RNA can induce both cellular and humoral immune responses in vivo. However, the use of RNA for clinical applications is greatly restricted especially by the short half life of RNA.

IVT vectors may be used in a standardized manner as template for in vitro transcription. Such IVT vectors may have the following structure: a 5' RNA polymerase promoter enabling RNA transcription, followed by a gene of interest which is flanked either 3' and/or 5' by untranslated regions (UTR), and a 3' polyadenyl cassette containing A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript.

The 3' poly(A) sequence of RNA is important for nuclear export, RNA stability and translational efficiency of eukaryotic messenger RNA (mRNA). The 3' poly(A) sequence is shortened over time and if short enough, the RNA is degraded enzymatically.

We have previously demonstrated that a 3' poly(A) sequence with a length of 120 nucleotides (A120) has a predominant effect on RNA stability and translational efficiency and thus, is beneficial for all-over RNA efficacy.

However, it has been observed that the DNA sequence encoding the 3' poly(A) sequence (3' polyadenyl cassette), i.e. a stretch of consecutive dA:dT base pairs, is subjected to shortening in some bacterial subclones, when propagated in *E. coli*. Accordingly, before producing the plasmid DNA as the starting material for in vitro transcription a large number of bacterial clones has to be tested, e.g., by determining the length of the 3' polyadenyl cassette by suitable restriction analysis, to obtain a single clone with a 3' polyadenyl cassette of the correct length encoding a 3' poly(A) sequence of the correct length.

It was the object of the present invention to find a 3' polyadenyl cassette which shows constant propagation with the coding plasmid DNA in *E. coli* and which encodes a 3' poly(A) sequence maintaining the effects with respect to supporting RNA stability and translational efficiency.

This object is achieved according to the invention by the subject matter of the claims.

According to the invention, it was found that a disruption of the 3' polyadenyl cassette (poly(dA:dT) region) by a 10 nucleotide random sequence, with an equal distribution of the 4 nucleotides (linker), has only minor influence on functionality of the encoded RNA but increases the stability of the 3' polyadenyl cassette in *E. coli*. Further, neither the sequence nor the position of the linker within the 3' poly(A) sequence resulted in a reduction of translational efficiency and stability of the in vitro transcribed RNA (IVT RNA).

For stability testing of the IVT vector region encoding the 3' poly(A) sequence, the SIINFEKL peptide (SEQ ID NO: 1) was cloned upstream of the poly(dA:dT) region. This construct showed a poly(dA:dT) instability (i.e. percentage of clones upon propagation with shortened poly(dA:dT)) of 50-60%. Detailed analysis, using the described restriction analysis method identified the region at position 30-50 as being particular sensitive to shortening of the poly(dA:dT) stretch. Introduction of a 10 nucleotide random sequence in this sensitive region led to an increase of the poly(dA:dT) stability. Constructs with 30 or 40 adenosine nucleotides, followed by the linker sequence and another 70 or 60 adenosines (A30L70 and A40L60) respectively, resulted in an poly(dA:dT) instability of only 3-4% in *E. coli*. Results were confirmed by testing the constructs in several different *E. coli* strains.

Functionality of IVT RNA encoded by DNA carrying the stabilized poly(dA:dT)-tails was tested in different assays. Electroporation of the IVT RNA in somatic cell lines but also in immune cells such as immature dendritic cells showed no difference in translational capacity compared to the A120 over a time period of 72 hours. Injection of luciferase encoding IVT RNA into mice confirmed an equal protein translation independent of the inserted type of the 3' poly(A) sequence.

An impact on the immunological response of the different 3' poly(A) sequences was analyzed by comparison of the amount of antigen-specific CD8$^+$ T-cells upon injection of SIINFEKL (SEQ ID NO: 1) IVT RNA. The experiments revealed no difference between the A120 and its stabilized versions A30L70 and A40L60.

Taken together, we show that the insertion of a 10 nucleotide random sequence between position 30 and 50 of a poly(dA:dT) region results in a more than 10-fold sequence stabilization in *E. coli*. The corresponding modified 3' poly(A) sequence of the RNA transcribed from the template DNA has the same functionality, i.e. stability and translational efficiency in vivo and in vitro as the classical A120. Additionally the immunological response is not altered by the use of a modified poly(A) sequence.

SUMMARY OF THE INVENTION

In one aspect, the invention relates to a nucleic acid molecule comprising in the 5'→3' direction of transcription:
(a) a promoter;
(b) a transcribable nucleic acid sequence or a nucleic acid sequence for introducing a transcribable nucleic acid sequence; and
(c) a nucleic acid sequence which, when transcribed under the control of the promoter (a), codes for a nucleotide sequence of at least 80 consecutive nucleotides in the transcript, wherein said nucleotide sequence of at least 80 consecutive nucleotides in the transcript is a polyadenyl sequence comprising within the polyadenyl sequence a sequence of one or more consecutive nucleotides containing nucleotides other than A nucleotides.

In one embodiment, said sequence of one or more consecutive nucleotides containing nucleotides other than A nucleotides is a sequence, preferably an arbitrary sequence, of 2 or more consecutive nucleotides, wherein the first and the last nucleotide of said sequence of 2 or more consecutive nucleotides is a nucleotide other than an A nucleotide.

In other words, the nucleic acid molecule of the invention contains 3' polyadenyl cassette (poly(dA:dT) region) containing at least one disruption by a sequence not encoding a sequence solely composed of A residues, i.e. the poly(dA:dT) region is disrupted by one or more stretches of basepairs comprising basepairs other than (dA:dT). Thus, the nucleic acid sequence (c), when transcribed under the control of the promoter (a), codes for a nucleotide sequence of at least 80 consecutive nucleotides in the transcript, wherein said nucleotide sequence of at least 80 consecutive nucleotides in the transcript is a polyadenyl sequence wherein at least one portion of the polyadenyl sequence is replaced by a sequence containing nucleotides other than A nucleotides such as a sequence of 2 or more consecutive nucleotides, wherein the first and the last nucleotide of said sequence of 2 or more nucleotides is a nucleotide other than an A nucleotide. In other words, the nucleic acid sequence (c), when transcribed under the control of the promoter (a), codes for a polyadenyl sequence containing interspersed within said polyadenyl sequence one or more sequence stretches of one or more nucleotides, wherein said sequence stretches each are not an A nucleotide or a stretch of A nucleotides, i.e. an oligo-A sequence or a poly-A sequence.

In one embodiment, said nucleic acid molecule is a DNA molecule. In one embodiment, said nucleic acid molecule is an expression vector or plasmid such as an IVT vector.

In one embodiment, said nucleic acid sequence (c) exhibits higher stability upon propagation of said nucleic acid molecule in *E. coli* compared to a nucleic acid molecule which comprises instead of said nucleic acid sequence (c) a nucleic acid sequence (c)' which, when transcribed under the control of the promoter (a), codes for a polyadenyl sequence of the same length as said nucleotide sequence of at least 80 consecutive nucleotides in the transcript.

In one embodiment, said nucleotide sequence of at least consecutive nucleotides comprises at least 90 nucleotides, preferably at least 100 nucleotides, preferably at least 110 nucleotides. In one embodiment, said nucleotide sequence of at least 80 consecutive nucleotides comprises about 120 nucleotides. In particular embodiments, said nucleotide sequence of at least 80 consecutive nucleotides comprises up to 200, preferably up to 150, and, in particular, up to 130 nucleotides. In one embodiment, at least 90%, preferably at least 92%, preferably at least 95%, 97% or 98% of the nucleotides of said nucleotide sequence of at least 80 consecutive nucleotides are A nucleotides in said polyadenyl sequence (not including A nucleotides in said sequence of one or more consecutive nucleotides containing nucleotides other than A nucleotides).

In one embodiment, said sequence of one or more consecutive nucleotides containing nucleotides other than A nucleotides is located within a region from position 21 to position 80, preferably from position 21 to position 60, more preferably from position 31 to position 50 of said polyadenyl sequence.

In one embodiment, said sequence of one or more consecutive nucleotides containing nucleotides other than A nucleotides is preceded by at least 20 A residues, preferably at least 30, 40 or 50 A residues in said polyadenyl sequence. In particular embodiments, said sequence of one or more consecutive nucleotides containing nucleotides other than A nucleotides is preceded by up to 80 A residues, preferably up to 70 or 60 A residues in said polyadenyl sequence.

In one embodiment, said sequence of one or more consecutive nucleotides containing nucleotides other than A nucleotides is followed by at least 20 A residues, preferably at least 30, 40, 50, 60 or 70 A residues in said polyadenyl sequence. In particular embodiments, said sequence of one or more consecutive nucleotides containing nucleotides other than A nucleotides is followed by up to 100 A residues, preferably up to 80 A residues in said polyadenyl sequence.

In one embodiment, said sequence of one or more consecutive nucleotides containing nucleotides other than A nucleotides is preceded by 20 to 50, preferably 30 to 40 A residues in said polyadenyl sequence and is followed by 30 to 80, preferably 40 to 70 A residues in said polyadenyl sequence.

In one embodiment, said sequence of one or more consecutive nucleotides containing nucleotides other than A nucleotides has a length of at least 3, at least 4, at least 5, at least 6, at least 8, preferably at least 10, more preferably at least 15 nucleotides.

In one embodiment, said sequence of one or more consecutive nucleotides containing nucleotides other than A nucleotides has a length of no more than 50, preferably no more than 30, more preferably no more than 20 nucleotides.

In one embodiment, said sequence of one or more consecutive nucleotides containing nucleotides other than A nucleotides does not comprise more than 3, preferably no more than 2, preferably no consecutive A residues.

In one embodiment, the nucleic acid sequences (b) and (c) under the control of the promoter (a) can be transcribed to give a common transcript.

In one embodiment, in the transcript said nucleotide sequence of at least 80 consecutive nucleotides is located at the 3' end.

In one embodiment, the nucleic acid molecule of the invention is a closed circular molecule or a linear molecule.

In one embodiment, the transcribable nucleic acid sequence comprises a nucleic acid sequence coding for a peptide or protein and the nucleic acid sequence for introducing a transcribable nucleic acid sequence is a multiple cloning site.

In one embodiment, the nucleic acid molecule of the invention further comprises one or more members selected from the group consisting of: (i) a reporter gene; (ii) a selectable marker; and (iii) an origin of replication.

In one embodiment, the nucleic acid molecule of the invention is suitable, in particular after linearization, for in vitro transcription of RNA, in particular mRNA.

Preferably, the nucleic acid sequence transcribed from the nucleic acid sequence (c), i.e., said nucleotide sequence of at least 80 consecutive nucleotides, is preferably active so as to increase the translation efficiency and/or the stability of the nucleic acid sequence transcribed from the transcribable nucleic acid sequence (b).

Prior to in vitro transcription, circular IVT vectors are generally linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. However, it was found that RNA having an open-ended poly(A) sequence is translated more efficiently than RNA having a poly(A) sequence with a masked terminus.

Accordingly, nucleic acid molecules of the invention when used as expression vectors preferably allow transcription of RNA with a poly(A) sequence which preferably has an open end in said RNA, i.e. no nucleotides other than A nucleotides flank said poly(A) sequence at its 3' end. An open-ended poly(A) sequence in the RNA can be achieved by introducing a type IIS restriction cleavage site into an expression vector which allows RNA to be transcribed under the control of a 5' RNA polymerase promoter and which contains a polyadenyl cassette, wherein the recognition sequence is located downstream of the polyadenyl cassette, while the cleavage site is located upstream and thus within the polyadenyl cassette. Restriction cleavage at the type IIS restriction cleavage site enables a plasmid to be linearized within the polyadenyl cassette. The linearized plasmid can then be used as template for in vitro transcription, the resulting transcript ending in an unmasked poly(A) sequence.

Accordingly, in one embodiment, it is preferred that the nucleic acid molecule of the invention can be cleaved, preferably enzymatically or in another biochemical way, within the nucleic acid sequence (c) in such a way that said cleavage results in a nucleic acid molecule which comprises, in the 5'→3' direction of transcription, the promoter (a), the nucleic acid sequence (b), and at least a part of the nucleic acid sequence (c), wherein the at least a part of the nucleic acid sequence (c), when transcribed under the control of the promoter (a), codes for said nucleotide sequence of at least 80 consecutive nucleotides in the transcript and wherein in the transcript the 3'-terminal nucleotide is an A nucleotide of said nucleotide sequence of at least 80 consecutive nucleotides.

Preferably, after cleavage, the nucleic acid molecule, at the end of the strand that serves as template for the nucleotide sequence of at least 80 consecutive nucleotides, has a T nucleotide which is part of the nucleic acid sequence which serves as template for the nucleotide sequence of at least 80 consecutive nucleotides in the transcript.

The nucleic acid molecule of the invention is preferably a closed circular molecule prior to cleavage and a linear molecule after cleavage.

Preferably, cleavage is carried out with the aid of a restriction cleavage site which is preferably a restriction cleavage site for a type IIS restriction endonuclease.

In one embodiment, the recognition sequence for the type IIS restriction endonuclease is located 5-26 base pairs, preferably 24-26 base pairs, downstream of the 3' end of the nucleic acid sequence (c).

In one embodiment, a nucleic acid molecule according to the invention is in a closed circular conformation and preferably suitable for in vitro transcription of RNA, in particular mRNA, in particular after linearization.

In further aspects, the invention relates to a nucleic acid molecule obtainable by linearization of an above-described nucleic acid molecule, preferably by cleavage within the nucleic acid sequence (c), and to RNA obtainable by transcription, preferably in vitro transcription, with above-described nucleic acid molecules under the control of the promoter (a).

In a further aspect, the invention relates to a method of propagating a nucleic acid molecule, comprising:
  (i) providing a nucleic acid molecule of the invention, and
  (ii) propagating said nucleic acid molecule in E. coli.

In one embodiment, propagating said nucleic acid molecule in E. coli comprises transforming E. coli with said nucleic acid molecule and cultivating said transformed E. coli.

In one embodiment, the method of the invention further comprises isolating said nucleic acid molecule from E. coli following propagation.

In a further aspect, the invention relates to a method of obtaining RNA, comprising:
  (i) propagating a nucleic acid molecule according to a method of the invention of propagating a nucleic acid molecule, and
  (ii) transcribing in vitro RNA using the nucleic acid molecule as a template.

In a further aspect, the invention relates to a method of obtaining a peptide or protein, comprising:
  (i) obtaining mRNA encoding the peptide or protein according to a method of the invention of obtaining RNA, and
  (ii) translating the mRNA.

In one embodiment, the method of obtaining RNA or the method of obtaining a peptide or protein further comprises, prior to transcription of the nucleic acid molecule, cleavage of the nucleic acid molecule.

In one embodiment, cleavage is within the nucleic acid sequence (c) in such a way that transcription of the nucleic acid obtained in this way generates a transcript which has at its 3'-terminal end said nucleotide sequence of at least 80 consecutive nucleotides, wherein the 3'-terminal nucleotide of said transcript is an A nucleotide of the nucleotide sequence of at least 80 consecutive nucleotides.

In all aspects of the methods according to the invention, cleavage is preferably carried out with the aid of a restriction cleavage site which is preferably a restriction cleavage site for a type IIS restriction endonuclease.

In one embodiment, the recognition sequence for the type IIS restriction endonuclease is 5-26 base pairs, preferably 24-26 base pairs, downstream of the 3' end of the nucleic acid sequence (c).

The invention also relates to RNA obtainable by the methods according to the invention of obtaining RNA.

The invention may be utilized, for example, for increasing expression of recombinant proteins in cellular transcription and expression. More specifically, it is possible, when producing recombinant proteins, to use expression vectors of the invention for transcription of recombinant nucleic acids and expression of recombinant proteins in cell-based systems. This includes, for example, the preparation of recombinant antibodies, hormones, cytokines, enzymes, and the like. This allows inter alia production costs to be reduced.

It is also possible to use the nucleic acid molecules of the invention for gene therapy applications. Accordingly, a nucleic acid molecule of the invention may be a gene therapy vector and used for expression of a transgene. To this end, any nucleic acid (DNA/RNA)-based vector systems (for example plasmids, adenoviruses, poxvirus vectors, influenza virus vectors, alphavirus vectors, and the like) may be used. Cells can be transfected with these vectors in vitro, for example in lymphocytes or dendritic cells, or else in vivo by direct administration.

RNA of the invention (obtained using a nucleic acid molecule described herein as a transcription template) may be employed, for example, for transient expression of genes, with possible fields of application being RNA-based vaccines which are transfected into cells in vitro or administered directly in vivo, transient expression of functional recombinant proteins in vitro, for example in order to initiate differentiation processes in cells or to study functions of proteins, and transient expression of functional recombinant proteins such as erythropoietin, hormones, coagulation inhibitors, etc., in vivo, in particular as pharmaceuticals.

RNA of the invention may be used in particular for transfecting antigen-presenting cells and thus as a tool for delivering the antigen to be presented and for loading antigen-presenting cells, with said antigen to be presented corresponding to the peptide or protein expressed from said RNA or being derived therefrom, in particular by way of intracellular processing such as cleavage, i.e. the antigen to be presented is, for example, a fragment of the peptide or protein expressed from the RNA. Such antigen-presenting cells may be used for stimulating T cells, in particular $CD4^+$ and/or $CD8^+$ T cells.

Accordingly, in a further aspect, the invention relates to a use of the RNA of the invention for transfecting a host cell. In one embodiment, the host cell is an antigen-presenting cell, in particular a dendritic cell, a monocyte or a macrophage.

In a further aspect, the invention relates to a use of the RNA of the invention for vaccination.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment a sequence of one or more consecutive nucleotides containing nucleotides other than A nucleotides is preceded by at least 20 A residues in said polyadenyl sequence and if in another preferred embodiment a sequence of one or more consecutive nucleotides containing nucleotides other than A nucleotides is followed by at least 20 A residues in said polyadenyl sequence, it is a contemplated preferred embodiment that a sequence of one or more consecutive nucleotides containing nucleotides other than A nucleotides is preceded and followed by at least 20 A residues in said polyadenyl sequence.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention describes nucleic acid molecules such as DNA plasmids useful as RNA expression vectors comprising a modified 3' poly(dA:dT) cassette (encoding a modified 3' poly(A) sequence) which shows constant propagation without being subject to shortening in *E. coli*.

*E. coli* is a gram-negative, facultatively anaerobic, rod-shaped bacterium of the genus *Escherichia* that is commonly found in the lower intestine of warm-blooded organisms. The bacterium can be grown easily and inexpensively in a laboratory setting, and has been intensively investigated for over 60 years. *E. coli* is the most widely studied prokaryotic model organism, and an important species in the fields of biotechnology and microbiology, where it has served as the host organism for the majority of work with recombinant DNA. *E. coli* strains according to the invention include: AG1, AB1157, B2155, BL21, BNN93, BNN97, BW26434, C600, CSH50, D1210, DB3.1, DH1, DH5α, DH10B, DH12S, DM1, *E. cloni*(r), *E. coli* K12 ER2738, ER2566, ER2267, HB101, IJ1126, IJ1127, JM83, JM101, JM103, JM105, JM106, JM107, JM108, JM109, JM110, JM2.300, LE392, Mach1, MC1061, MC4100, MFDpir, MG1655, OmniMAX2, RR1, RV308, SOLR, SS320, STBL2, STBL3, STBL4, SURE, SURE2, TG1, TOP10, Top10F', W3110, WM3064, XL1-Blue, XL2-Blue, XL1-Red and XL10-Gold.

According to the invention, a nucleic acid molecule or a nucleic acid sequence refers to a nucleic acid which is preferably deoxyribonucleic acid (DNA) or ribonucleic acid (RNA). According to the invention, nucleic acids comprise genomic DNA, cDNA, mRNA, recombinantly prepared and chemically synthesized molecules. According to the invention, a nucleic acid may be in the form of a single-stranded or double-stranded and linear or covalently closed circular molecule.

In the context of the present invention, the term "RNA" relates to a molecule which comprises ribonucleotide residues and preferably being entirely or substantially composed of ribonucleotide residues. The term "ribonucleotide" relates to a nucleotide with a hydroxyl group at the 2'-position of a β-D-ribofuranosylgroup. The term "RNA" comprises double-stranded RNA, single stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs, particularly analogs of naturally-occurring RNAs. According to the invention, RNA includes mRNA.

The term "mRNA" means "messenger-RNA" and relates to a transcript which is generated by using a DNA template and encodes a peptide or protein. Typically, mRNA comprises a 5'-UTR, a protein coding region, and a 3'-UTR. mRNA may be generated by in vitro transcription from a DNA template. The in vitro transcription methodology is known to the skilled person. For example, there is a variety of in vitro transcription kits commercially available. According to the invention, mRNA may be modified by further stabilizing modifications and capping, in addition to the modifications according to the invention.

In one embodiment, the term "modification" relates to providing a RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell. Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be generated post-transcriptionally using capping enzymes, for example, capping enzymes of vaccinia virus.

The term "nucleic acid" according to the invention also comprises a chemical derivatization of a nucleic acid on a nucleotide base, on the sugar or on the phosphate, and nucleic acids containing non-natural nucleotides and nucleotide analogs.

According to the invention, a "nucleic acid sequence which is derived from a nucleic acid sequence" refers to a nucleic acid containing, in comparison with the nucleic acid from which it is derived, single or multiple nucleotide substitutions, deletions and/or additions. Preferably there is a certain degree of homology between said nucleic acids and the nucleotide sequences of said nucleic acids correspond in a significant direct or complementary manner. According to the invention, a nucleic acid derived from a nucleic acid has a functional property of the nucleic acid from which it is derived. Such functional properties include in particular the ability to increase, in a functional linkage to a nucleic acid which can be transcribed into RNA (transcribable nucleic acid sequence), the stability and/or translation efficiency of RNA produced from this nucleic acid in the complete RNA molecule.

According to the invention, "functional linkage" or "functionally linked" relates to a connection within a functional relationship. A nucleic acid is "functionally linked" if it is functionally related to another nucleic acid sequence. For example, a promoter is functionally linked to a coding sequence if it influences transcription of said coding sequence. Functionally linked nucleic acids are typically adjacent to one another, where appropriate separated by further nucleic acid sequences, and, in particular embodiments, are transcribed by RNA polymerase to give a single RNA molecule (common transcript).

The nucleic acids described according to the invention are preferably isolated. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant DNA techniques.

A nucleic acid is "complementary" to another nucleic acid if the two sequences can hybridize with one another and form a stable duplex, said hybridization being carried out preferably under conditions which allow specific hybridization between polynucleotides (stringent conditions). Stringent conditions are described, for example, in Molecular Cloning: A Laboratory Manual, J. Sambrook et al., eds., 2nd edition, Cold Spring Harbor Laboratory Press, Cold Spring Harbor, N.Y. 1989 or Current Protocols in Molecular Biology, F. M. Ausubel et al., eds., John Wiley & Sons, Inc., New York, and refer, for example, to a hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred, is washed, for example, in 2×SSC at room temperature and then in 0.1-0.5×SSC/0.1×SDS at temperatures up to 68° C.

According to the invention, homologous nucleic acids have nucleotides which are at least 60%, at least 70%, at least 80%, at least 90%, and preferably at least 95%, at least 98% or at least 99%, identical.

The term "% identical" is intended to refer to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

"3' end of a nucleic acid" refers according to the invention to that end which has a free hydroxy group. In a diagrammatic representation of double-stranded nucleic acids, in particular DNA, the 3' end is always on the right-hand side. "5' end of a nucleic acid" refers according to the invention to that end which has a free phosphate group. In a diagrammatic representation of double-strand nucleic acids, in particular DNA, the 5' end is always on the left-hand side.

```
5' end      5'--P-NNNNNNN-OH-3'      3' end
            3'-HO-NNNNNNN-P--5'
```

In particular embodiments, a nucleic acid is functionally linked according to the invention to expression control sequences which may be homologous or heterologous with respect to the nucleic acid.

A transcribable nucleic acid sequence, in particular a nucleic acid sequence coding for a peptide or protein, and an expression control sequence are "functionally" linked to one another, if they are covalently linked to one another in such a way that transcription or expression of the transcribable and in particular coding nucleic acid sequence is under the control or under the influence of the expression control sequence. If the nucleic acid sequence is to be translated into a functional peptide or protein, induction of an expression control sequence functionally linked to the coding sequence results in transcription of said coding sequence, without causing a frame shift in the coding sequence or the coding sequence being unable to be translated into the desired peptide or protein.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively, such as TATA box, capping sequence, CAAT sequence and the like. More specifically, 5'-untranscribed expression control sequences include a promoter region which encompasses a promoter sequence for transcription control of the functionally linked gene. Expression control sequences may also include enhancer sequences or upstream activator sequences.

The nucleic acid sequences specified herein, in particular transcribable and coding nucleic acid sequences, may be combined with any expression control sequences, in particular promoters, which may be homologous or heterologous to said nucleic acid sequences, with the term "homologous" referring to the fact that a nucleic acid sequence is also functionally linked naturally to the expression control sequence, and the term "heterologous" referring to the fact that a nucleic acid sequence is not naturally functionally linked to the expression control sequence.

The term "promoter" or "promoter region" refers to a DNA sequence upstream (5') of the coding sequence of a gene, which controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

Examples of promoters preferred according to the invention are promoters for SP6, T3 or T7 polymerase.

According to the invention, the term "expression" is used in its most general meaning and comprises production of RNA or of RNA and protein. It also comprises partial expression of nucleic acids. Furthermore, expression may be transient or stable. With respect to RNA, the term "expression" or "translation" relates to the process in the ribosomes of a cell by which a strand of messenger RNA directs the assembly of a sequence of amino acids to make a peptide or protein.

The term "nucleic acid sequences which can be transcribed to give a common transcript" means that said nucleic acid sequences are functionally linked to one another in such a way that, where appropriate after linearization such as restriction enzyme cleavage of the nucleic acid molecule comprising said nucleic acid sequences, in particular of a closed circular nucleic acid molecule, transcription under the control of a promoter results in an RNA molecule comprising the transcripts of said nucleic acid sequences covalently bound to one another, where appropriate separated by sequences located inbetween.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system. Preferably, cloning vectors are applied for the generation of transcripts. These cloning vectors are generally designated as transcription vectors and are according to the present invention encompassed by the term "vector". According to the present invention, RNA preferably is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

The term "nucleic acid sequence transcribed from a nucleic acid sequence" refers to RNA, where appropriate as part of a complete RNA molecule, which is a transcription product of the latter nucleic acid sequence.

The term "nucleic acid sequence which is active in order to increase the translation efficiency and/or stability of a nucleic acid sequence" means that the first nucleic acid sequence is capable of modifying, in a common transcript with the second nucleic acid sequence, the translation efficiency and/or stability of said second nucleic acid sequence in such a way that said translation efficiency and/or stability is increased in comparison with the translation efficiency and/or stability of said second nucleic acid sequence without said first nucleic acid sequence. In this context, the term "translation efficiency" relates to the amount of translation product provided by an RNA molecule within a particular period of time and the term "stability" relates to the half life of an RNA molecule.

It has been demonstrated that a double 3'-untranslated region (UTR), in particular of the human beta-globin gene, in an RNA molecule improves translation efficiency in a way which clearly exceeds the total effect to be expected using two individual UTRs.

Modification, and thereby stabilization and/or increase in translation efficiency, of RNA can be achieved according to the invention by genetically modifying expression nucleic acid molecules of the invention when used as expression vectors in such a way that they allow transcription of RNA with two or more 3'-untranslated regions at its 3' end, and preferably between the sequence coding for a peptide or protein (open reading frame) and the poly(A) sequence or the poly(A) sequence comprising a sequence of one or more consecutive nucleotides containing nucleotides other than A nucleotides.

Accordingly, a nucleic acid molecule of the invention may comprise, preferably between the nucleic acid sequence (b) and the nucleic acid sequence (c) two or more nucleic acid sequences, each of said two or more nucleic acid sequences corresponding to the 3'-untranslated region of a gene or being derived therefrom. Said two or more nucleic acid sequences may be identical or different. In preferred embodiments, said two or more nucleic acid sequences are independently of one another derived from a gene selected from the group consisting of globin genes such as alpha2-globin, alpha1-globin, beta-globin and growth hormone, preferably human beta-globin.

The 3'-untranslated region relates to a region which is located at the 3' end of a gene, downstream of the termination codon of a protein-encoding region, and which is transcribed but is not translated into an amino acid sequence.

According to the invention, a first polynucleotide region is considered to be located downstream of a second polynucleotide region, if the 5' end of said first polynucleotide region is the part of said first polynucleotide region closest to the 3' end of said second polynucleotide region.

The 3'-untranslated region typically extends from the termination codon for a translation product to the poly(A) sequence which is usually attached after the transcription process. The 3'-untranslated regions of mammalian mRNA typically have a homology region known as the AAUAAA hexanucleotide sequence. This sequence is presumably the poly(A) attachment signal and is frequently located from 10 to 30 bases upstream of the poly(A) attachment site.

3'-untranslated regions may contain one or more inverted repeats which can fold to give stem-loop structures which act as barriers for exoribonucleases or interact with proteins known to increase RNA stability (e.g. RNA-binding proteins).

5'- and/or 3'-untranslated regions may, according to the invention, be functionally linked to a transcribable and in particular coding nucleic acid, so as for these regions to be associated with the nucleic acid in such a way that the stability and/or translation efficiency of the RNA transcribed from said transcribable nucleic acid are increased.

The 3'-untranslated regions of immunoglobulin mRNAs are relatively short (fewer than about 300 nucleotides), while the 3'-untranslated regions of other genes are relatively long. For example, the 3'-untranslated region of tPA is about 800 nucleotides in length, that of factor VIII is about 1800 nucleotides in length and that of erythropoietin is about 560 nucleotides in length.

It can be determined according to the invention, whether a 3'-untranslated region or a nucleic acid sequence derived therefrom increases the stability and/or translation efficiency of RNA, by incorporating the 3'-untranslated region or the nucleic acid sequence derived therefrom into the 3'-untranslated region of a gene and measuring whether said incorporation increases the amount of protein synthesized.

The above applies accordingly to the case in which according to the invention a nucleic acid comprises two or more 3'-untranslated regions which are preferably coupled sequentially with or without a linker inbetween, preferably in a "head-to-tail relationship" (i.e. the 3'-untranslated regions have the same orientation, preferably the orientation naturally occurring in a nucleic acid).

According to the invention, the term "gene" refers to a particular nucleic acid sequence which is responsible for producing one or more cellular products and/or for achieving one or more intercellular or intracellular functions. More specifically, said term relates to a DNA section which comprises a nucleic acid coding for a specific protein or a functional or structural RNA molecule.

Polyadenylation is the addition of a poly(A) sequence or tail to a primary transcript RNA. The poly(A) sequence consists of multiple adenosine monophosphates. In other words, it is a stretch of RNA that has only adenine bases. In eukaryotes, polyadenylation is part of the process that produces mature messenger RNA (mRNA) for translation. It, therefore, forms part of the larger process of gene expression. The process of polyadenylation begins as the transcription of a gene finishes, or terminates. The 3'-most segment of the newly made pre-mRNA is first cleaved off by a set of proteins; these proteins then synthesize the poly(A) sequence at the RNA's 3' end. The poly(A) sequence is important for the nuclear export, translation, and stability of mRNA. The sequence is shortened over time, and, when it is short enough, the mRNA is enzymatically degraded.

The terms "polyadenyl sequence", "poly(A) sequence" or "poly(A) tail" refer to a sequence of adenyl residues which is typically located at the 3' end of an RNA molecule. The invention provides for such a sequence to be attached during RNA transcription by way of a DNA template on the basis of repeated thymidyl residues in the strand complementary to the coding strand, whereas said sequence is normally not encoded in the DNA but is attached to the free 3' end of the RNA by a template-independent RNA polymerase after transcription in the nucleus. The term "A nucleotides" or "A" refers to adenyl residues.

In a preferred embodiment, a nucleic acid molecule according to the invention is a vector. The term "vector" is used here in its most general meaning and comprises any intermediate vehicles for a nucleic acid which, for example, enable said nucleic acid to be introduced into prokaryotic and/or eukaryotic host cells and, where appropriate, to be integrated into a genome. Such vectors are preferably replicated and/or expressed in the cell. Vectors comprise plasmids, phagemids or virus genomes. The term "plasmid", as used herein, generally relates to a construct of extrachromosomal genetic material, usually a circular DNA duplex, which can replicate independently of chromosomal DNA.

According to the invention, the term "host cell" refers to any cell which can be transformed or transfected with an exogenous nucleic acid. The term "host cell" comprises, according to the invention, prokaryotic (e.g. *E. coli*) or eukaryotic cells (e.g. yeast cells and insect cells). Particular preference is given to mammalian cells such as cells from humans, mice, hamsters, pigs, goats, primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, in particular a dendritic cell, a monocyte or a macrophage. A nucleic acid may be present in the host cell in a single or in several copies and, in one embodiment is expressed in the host cell.

According to the present invention, the term "peptide" comprises oligo- and polypeptides and refers to substances which comprise two or more, preferably 3 or more, preferably 4 or more, preferably 6 or more, preferably 8 or more, preferably 10 or more, preferably 13 or more, preferably 16 or more, preferably 20 or more, and up to preferably 50, preferably 100 or preferably 150, consecutive amino acids linked to one another via peptide bonds.

The term "protein" refers to large peptides, preferably peptides having at least 151 amino acids, but the terms "peptide" and "protein" are used herein usually as synonyms. The terms "peptide" and "protein" comprise according to the invention substances which contain not only amino acid components but also non-amino acid components such as sugars and phosphate structures, and also comprise substances containing bonds such as ester, thioether or disulfide bonds.

According to the present invention, a nucleic acid such as RNA may encode a peptide or protein. Accordingly, a transcribable nucleic acid sequence or a transcript thereof may contain an open reading frame (ORF) encoding a peptide or protein. Said nucleic may express the encoded peptide or protein. For example, said nucleic acid may be a nucleic acid encoding and expressing an antigen or a pharmaceutically active peptide or protein such as an immunologically active compound (which preferably is not an antigen).

According to the invention, the term "nucleic acid encoding a peptide or protein" means that the nucleic acid, if present in the appropriate environment, preferably within a cell, can direct the assembly of amino acids to produce the peptide or protein during the process of translation. Preferably, RNA according to the invention is able to interact with the cellular translation machinery allowing translation of the peptide or protein.

According to the invention, in one embodiment, RNA comprises or consists of pharmaceutically active RNA. A "pharmaceutically active RNA" may be RNA that encodes a pharmaceutically active peptide or protein.

A "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., administration of the peptide or protein to a subject elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases. Immunologically active compounds can be useful as vaccine adjuvants.

If, according to the present invention, it is desired to induce or enhance an immune response by using RNA as described herein, the immune response may be triggered or enhanced by the RNA. For example, proteins or peptides encoded by the RNAs or procession products thereof may be presented by major histocompatibility complex (MHC) proteins expressed on antigen presenting cells. The MHC peptide complex can then be recognized by immune cells such as T cells leading to their activation.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases.

According to the invention, the term "disease" also refers to cancer diseases. The terms "cancer disease" or "cancer" (medical term: malignant neoplasm) refer to a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. Examples of cancers include, but are not limited to, carcinoma, lymphoma, blastoma, sarcoma, glioma and leukemia. More particularly, examples of such cancers include bone cancer, blood cancer, lung cancer, liver cancer, pancreatic cancer, skin cancer, cancer of the head or neck, cutaneous or intraocular malignant melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases.

The term "infectious disease" refers to any disease which can be transmitted from individual to individual or from organism to organism, and is caused by a microbial agent (e.g. common cold). Examples of infectious diseases include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), and severe acute respiratory syndrome (SARS), bacterial infectious diseases, such as Legionnaire's disease (*Legionella*), sexually transmitted diseases (e.g. chlamydia or gonorrhea), gastric ulcer (*Helicobacter*), cholera (*Vibrio*), tuberculosis, diphtheria, infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and Toxoplasma; or fungal infections, which are caused e.g. by *Cryptococcus neoformans, Histoplasma capsulatum, Coccidioides immitis, Blastomyces dermatitidis* or *Candida albicans*.

The term "autoimmune disease" refers to any disease in which the body produces an immunogenic (i.e. immune system) response to some constituent of its own tissue. In other words, the immune system loses its ability to recognize some tissue or system within the body as self and targets and attacks it as if it were foreign. Autoimmune diseases can be classified into those in which predominantly one organ is affected (e.g. hemolytic anemia and anti-immune thyroiditis), and those in which the autoimmune disease process is diffused through many tissues (e.g. systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

According to the invention, an immune response may be stimulated by introducing into a subject a suitable mRNA which codes for an antigen or a fragment thereof, e.g., a disease-associated antigen.

The term "antigen" relates to an agent comprising an epitope against which an immune response is to be generated. The term "antigen" includes in particular proteins, peptides, polysaccharides, nucleic acids, especially RNA and DNA, and nucleotides. The term "antigen" also includes agents, which become antigenic—and sensitizing—only through transformation (e.g. intermediately in the molecule or by completion with body protein). An antigen is preferably presentable by cells of the immune system such as antigen presenting cells like dendritic cells or macrophages. In addition, an antigen or a processing product thereof is preferably recognizable by a T or B cell receptor, or by an immunoglobulin molecule such as an antibody. In a preferred embodiment, the antigen is a disease-associated antigen, such as a tumor-associated antigen, a viral antigen, or a bacterial antigen.

The term "disease-associated antigen" is used in it broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen may therefore be used for therapeutic purposes. Disease-associated antigens are preferably associated with infection by microbes, typically microbial antigens, or associated with cancer, typically tumors.

The term "disease involving an antigen" refers to any disease which implicates an antigen, e.g. a disease which is characterized by the presence of an antigen. The disease involving an antigen can be an infectious disease, an autoimmune disease, or a cancer disease or simply cancer. As mentioned above, the antigen may be a disease-associated antigen, such as a tumor-associated antigen, a viral antigen, or a bacterial antigen.

In one embodiment, a disease-associated antigen is a tumor-associated antigen. In this embodiment, the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigens or fragments thereof such as MHC class I and class II peptides or nucleic acids, in particular mRNA, encoding such antigen or fragment makes it possible to elicit a MHC class I and/or a class II type response and, thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I-presented peptides by transfection with nucleic acids encoding tumor antigens in vitro and administered to a patient. In one embodiment, the term "tumor-associated antigen" refers to a constituent of cancer cells which may be derived from the cytoplasm, the cell surface and the cell nucleus. In particular, it refers to those antigens which are produced, preferably in large quantity, intracellularly or as surface antigens on tumor cells. Examples for tumor antigens include HER2, EGFR, VEGF, CAMPATH1-antigen, CD22, CA-125, HLA-DR, Hodgkin-lymphoma or mucin-1, but are not limited thereto.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably not or only rarely expressed in normal tissues or is mutated in tumor cells. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the Claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "immune response", as used herein, relates to a reaction of the immune system such as to immunogenic organisms, such as bacteria or viruses, cells or substances. The term "immune response" includes the innate immune response and the adaptive immune response. Preferably, the immune response is related to an activation of immune cells, an induction of cytokine biosynthesis and/or antibody production. It is preferred that the immune response comprises the steps of activation of antigen presenting cells, such as dendritic cells and/or macrophages, presentation of an antigen or fragment thereof by said antigen presenting cells and activation of cytotoxic T cells due to this presentation.

The term "treat" or "treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

In particular, the term "treatment of a disease" includes curing, shortening the duration, ameliorating, slowing down or inhibiting progression or worsening of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject" or "individual", as used herein, preferably relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity, such as animals of zoos. In a preferred embodiment, the subject is a human.

The term "antigen presenting cell" (APC) relates to a cell of a variety of cells capable of displaying, acquiring, and/or presenting at least one antigen or antigenic fragment on (or at) its cell surface.

Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

In one embodiment of the invention, nucleic acids such as RNA are administered to a patient by ex vivo methods, i.e. by removing cells from a patient, genetically modifying said cells and reintroducing the modified cells into the patient. Transfection and transduction methods are known to the skilled worker.

According to the invention, the term "transfection" refers to introducing one or more nucleic acids into an organism or into a host cell. Various methods may be employed in order to introduce according to the invention nucleic acids into cells in vitro or in vivo. Such methods include transfection of nucleic acid-CaPO$_4$ precipitates, transfection of nucleic acids associated with DEAE, transfection or infection with viruses carrying the nucleic acids of interest, liposome-mediated transfection, and the like.

According to the invention, nucleic acids may be directed to particular cells. In such embodiments, a carrier used for administering a nucleic acid to a cell (e.g. a retrovirus or a liposome) may have a bound targeting molecule. For example, a molecule such as an antibody specific to a surface membrane protein on the target cell, or a ligand for a receptor on the target cell may be incorporated into or bound to the nucleic acid carrier. If administration of a nucleic acid by liposomes is desired, proteins binding to a surface membrane protein associated with endocytosis may be incorporated into the liposome formulation in order to enable targeting and/or absorption. Such proteins include capsid proteins or fragments thereof which are specific to a particular cell type, antibodies to proteins that are internalized, proteins targeting an intracellular site, and the like.

"Reporter" relates to a molecule, typically a peptide or protein, which is encoded by a reporter gene and measured in a reporter assay. Conventional systems usually employ an enzymatic reporter and measure the activity of said reporter.

The term "multiple cloning site" refers to a nucleic acid region containing restriction enzyme sites, any one of which may be used for cleavage of, for example, a vector and insertion of a nucleic acid.

According to the invention, two elements such as nucleotides or amino acids are consecutive, if they are directly adjacent to one another, without any interruption. For example, a sequence of x consecutive nucleotides N refers to the sequence $(N)_x$.

"Restriction endonuclease" or "restriction enzyme" refers to a class of enzymes that cleave phosphodiester bonds in both strands of a DNA molecule within specific base sequences. They recognize specific binding sites, referred to as recognition sequences, on a double-stranded DNA molecule. The sites at which said phosphodiester bonds in the DNA are cleaved by said enzymes are referred to as cleavage sites. In the case of type IIS enzymes, the cleavage site is located at a defined distance from the DNA binding site. According to the invention, the term "restriction endonuclease" comprises, for example, the enzymes SapI, EciI, BpiI, AarI, AloI, BaeI, BbvCI, PpiI and PsrI, BsrD1, BtsI, EarI, BmrI, BsaI, BsmBI, FauI, BbsI, BciVI, BfuAI, BspMI, BseRI, EciI, BtgZI, BpuEI, BsgI, MmeI, CspCI, BaeI, BsaMI, Mva1269I, PctI, Bse3DI, BseMI, Bst6I, Eam1104I, Ksp632I, BfiI, Bso31I, BspTNI, Eco31I, Esp3I, BfuI, Acc36I, AarI, Eco57I, Eco57MI, GsuI, AloI, Hin4I, PpiI, and PsrI.

The term "stability" of RNA relates to the "half-life" of RNA. "Half-life" relates to the period of time which is needed to eliminate half of the activity, amount, or number of molecules. In the context of the present invention, the half-life of a RNA is indicative for the stability of said RNA.

The nucleic acids such as RNA described herein, in particular when used for the treatments described herein, may be present in the form of a pharmaceutical composition or kit comprising the nucleic acid and optionally one or more pharmaceutically acceptable carriers, diluents and/or excipients.

Pharmaceutical compositions are preferably sterile and contain an effective amount of the nucleic acid.

Pharmaceutical compositions are usually provided in a uniform dosage form and may be prepared in a manner known in the art. The pharmaceutical composition may, e.g., be in the form of a solution or suspension.

The pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interfere with the action of the active component(s) of the pharmaceutical composition.

Salts which are not pharmaceutically acceptable may be used for preparing pharmaceutically acceptable salts and are included in the invention. Pharmaceutically acceptable salts of this kind comprise, in a non-limiting way, those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition include acetic acid in a salt, citric acid in a salt, boric acid in a salt and phosphoric acid in a salt.

Suitable preservatives for use in the pharmaceutical composition include benzalkonium chloride, chlorobutanol, paraben and thimerosal.

The term "carrier" refers to an organic or inorganic component, of a natural or non-natural (synthetic) nature, with which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are, e.g., sterile water, glucose solutions, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxy-propylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The pharmaceutical compositions described herein may be administered via any conventional route, such as by parenteral administration including by injection or infusion. Administration is preferably parenterally, e.g. intravenously, intraarterially, subcutaneously, in the lymph node, intradermally or intramuscularly.

Compositions suitable for parenteral administration usually comprise a sterile aqueous or non-aqueous preparation of the active compound, which is preferably isotonic to the blood of the recipient. Examples of compatible carriers and solvents are Ringer's solution and isotonic sodium chloride solution. In addition, usually sterile, fixed oils are used as solution or suspension medium.

The agents and compositions described herein are preferably administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors.

Accordingly, the doses administered of the agents described herein may depend on several of these parameters. In the case that a reaction in a patient is insufficient with an initial dose, higher doses (or effectively higher doses achieved by a different, more localized route of administration) may be used.

The present invention is described in detail by the following figures and examples which should be construed by way of illustration only and not by way of limitation. On the basis of the description and the examples, further embodiments are accessible to the skilled worker and are likewise within the scope of the invention.

FIGURES

Figure 1B:
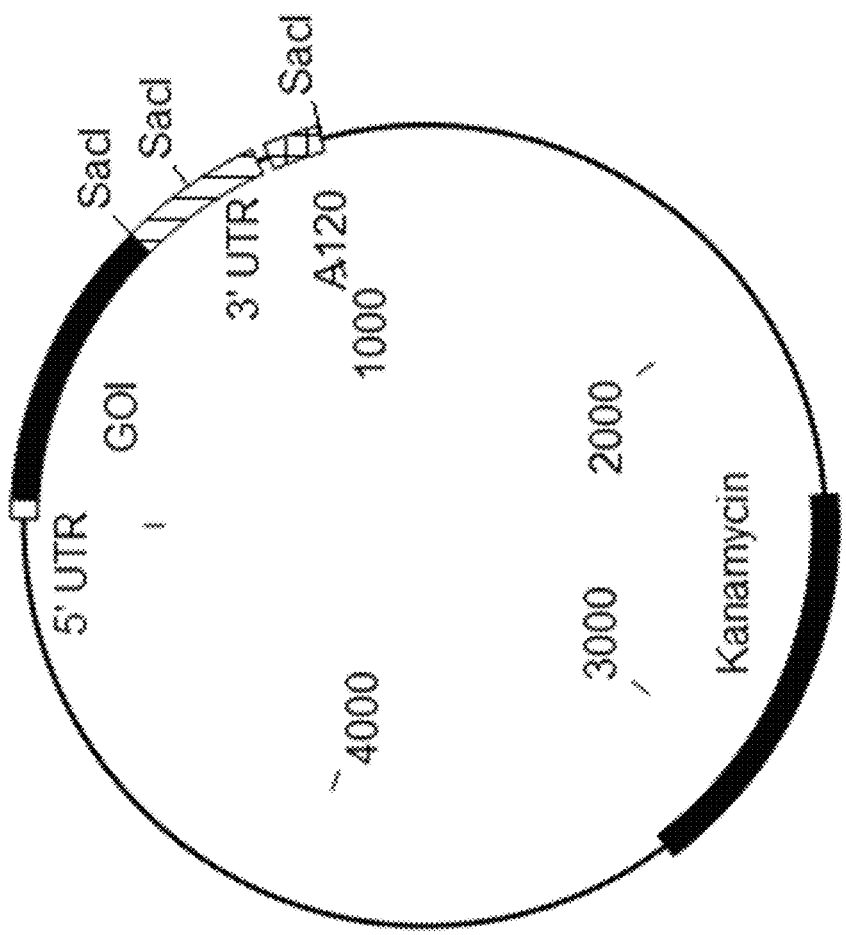

FIGS. 1A-1B: Semi-Automated Screen on Poly(dA:dT) Stability

96 E. coli clones carrying a plasmid DNA with a poly (dA:dT)-region were picked and inoculated in 1.4 mL in a 96 well plate for 14-16 h (37° C., 225 rpm). Bacterial culture suspensions were harvested and plasmid DNA was purified using a Nucleospin 96 well kit (Macherey & Nagel) according to the manufacturer's protocol. Plasmid DNA concentration was determined by UV spectroscopy (Nanodrop 2000, Thermo Scientific). Poly(dA:dT) integrity was determined by SacI restriction analysis (New England Biolabs). The resulting fragments were resolved on an automated capillary gel electrophoresis (Qiagen). FIG. 1A) Example of the poly(dA:dT) analysis of 8 clones. The bands of the internal size marker at 25 bp and 500 bp are marked with black asterisks. The expected bands for a poly(dA:dT) sequence of the correct length at 142 bp and 270 bp are marked with black arrows. Clone 1 and clone 4 show an additional band resulting from a shortened poly(dA:dT) sequence, marked with red asterisks. FIG. 1B) Example of a vector map coding for a mRNA consisting of a 5'-untranslated region (5UTR), a gene of interest (GOI), the 3'-untranslated region (3UTR) and the poly(A) tail (A120). The SacI restriction sites are depicted and the lengths of the fragments upon incubation with SacI are given.

Figure 2:
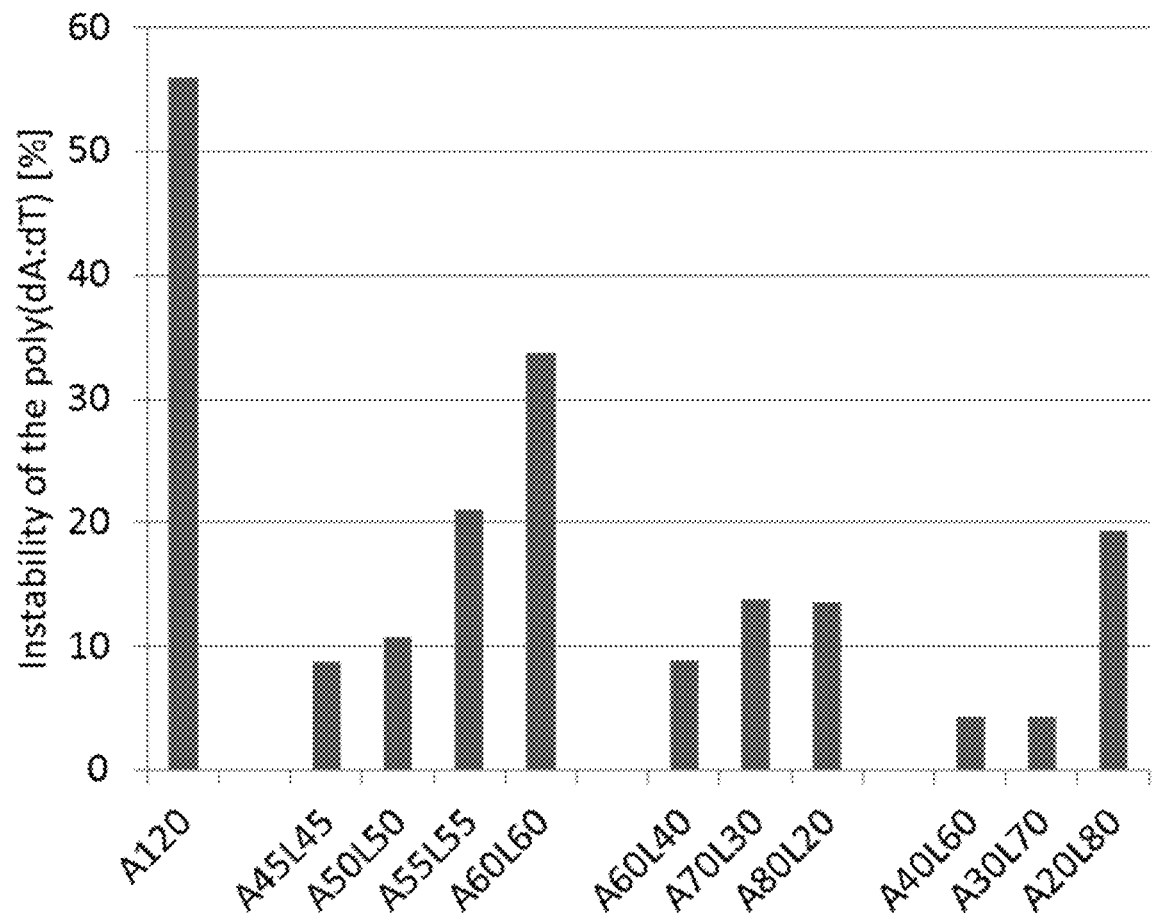

FIG. 2: Stability of Different Poly(dA:dT) Constructs

Plasmid DNA of 96 E. coli clones of each poly(dA:dT) construct was purified and SacI restriction analysis was performed. Construct names: A+numbers: number of adenosines 5' of the linker sequence+L: linker sequence+ number: number of adenosines 3' of the linker sequence. Clones with shortened poly(dA:dT) sequence were determined and are given as percent of the total number of E. coli clones.

Figure 3:
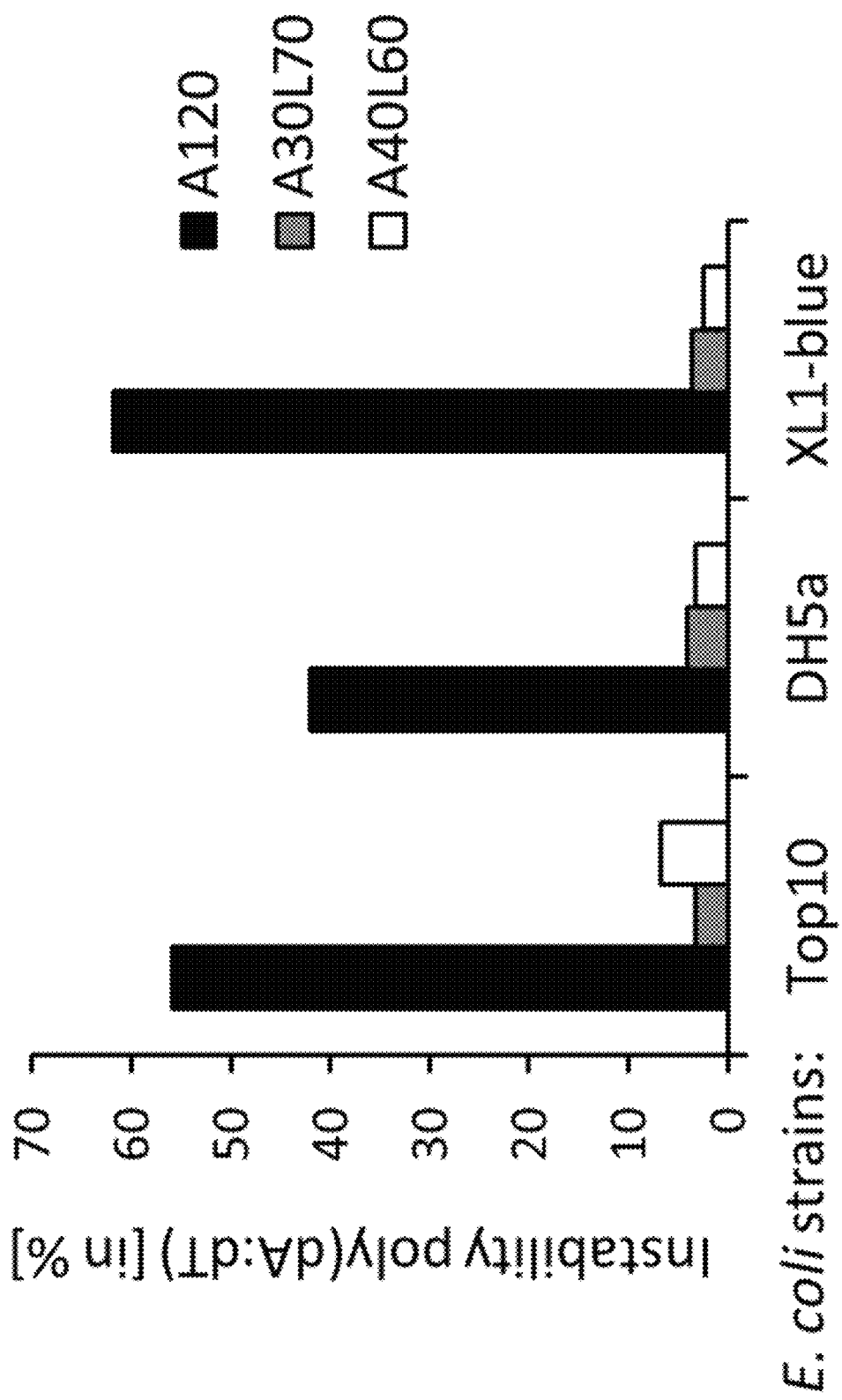

FIG. 3: Stability of Poly(dA:dT) Constructs in Different E. Coli Strains

E. coli strains TOP10, DH5α and XL1-blue were used for poly(dA:dT) integrity testing by SacI restriction analysis. 96 clones for the constructs A120, A30L70 and A40L60 were tested. Number of clones with shortened poly(dA:dT) sequence are given in percent of total.

Figure 4B:
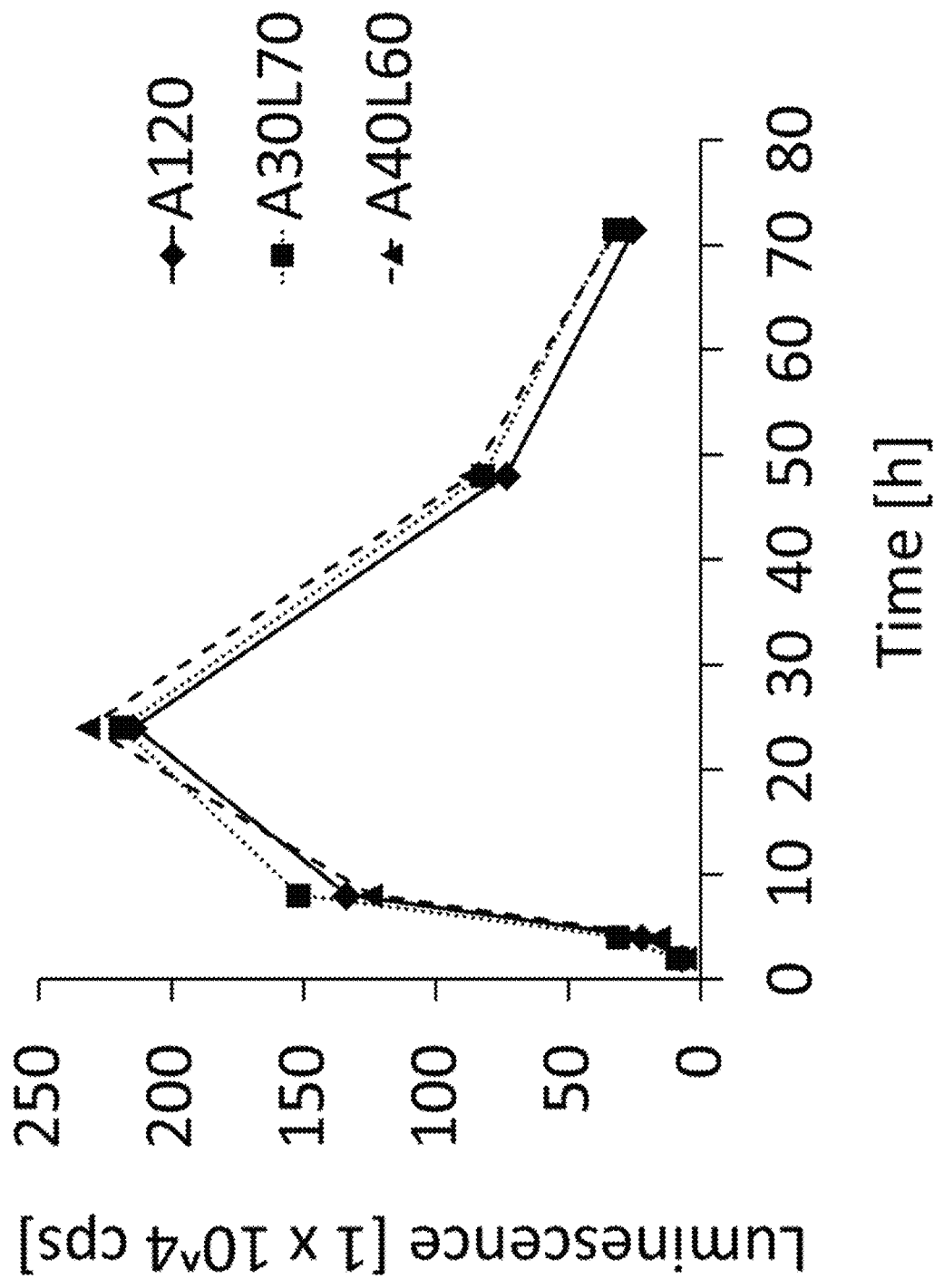

FIGS. 4A-4C: Functional In Vitro Characterization of Different Poly(A)-Tails

The plasmids coding for the firefly luciferase gene containing either A120, A30L70 or A40L60 were linearized downstream of the poly(dA:dT) with a classIIS restriction enzyme thereby generating a template with no additional nucleotide past the poly(dA:dT). Linearized plasmid DNA was purified using carboxylated magnetic beads (Invitrogen), quantified spectrophotometrically and subjected to in vitro transcriptions. For in vitro transcriptions T7 RNA polymerase (Fermentas), the respective reaction buffer and 6 mM NTPs were used. For efficient capping of the RNA the GTP concentration was lowered to 1.5 mM and 6 mM of β-S-ARCA(D2) were added to the reaction and incubated for 2.5 h at 37° C. RNA was purified via carboxylated magnetic beads (Invitrogen) and RNA concentration and quality were assessed by spectrophotometry and analysis on a 2100 Bionanalyzer (Agilent). FIG. 4A) 1×10⁶ human immature dendritic cells (iDC), FIG. 4B) human fibroblasts (CCD) or FIG. 4C) murine myoblastoma cells (C2C12) cells were mixed with 10 pmol of RNA respectively and subjected to electroporation. 5×10⁴ cells were seeded in X-VIVO15 media (Lonza) with additives in 24 well dishes. At 2, 4, 8, 24, 48 and 72 hours after seeding firefly luciferase activities were determined by addition of Luciferin (Promega) in a fluorescence reader (TECAN).

Figure 5A:
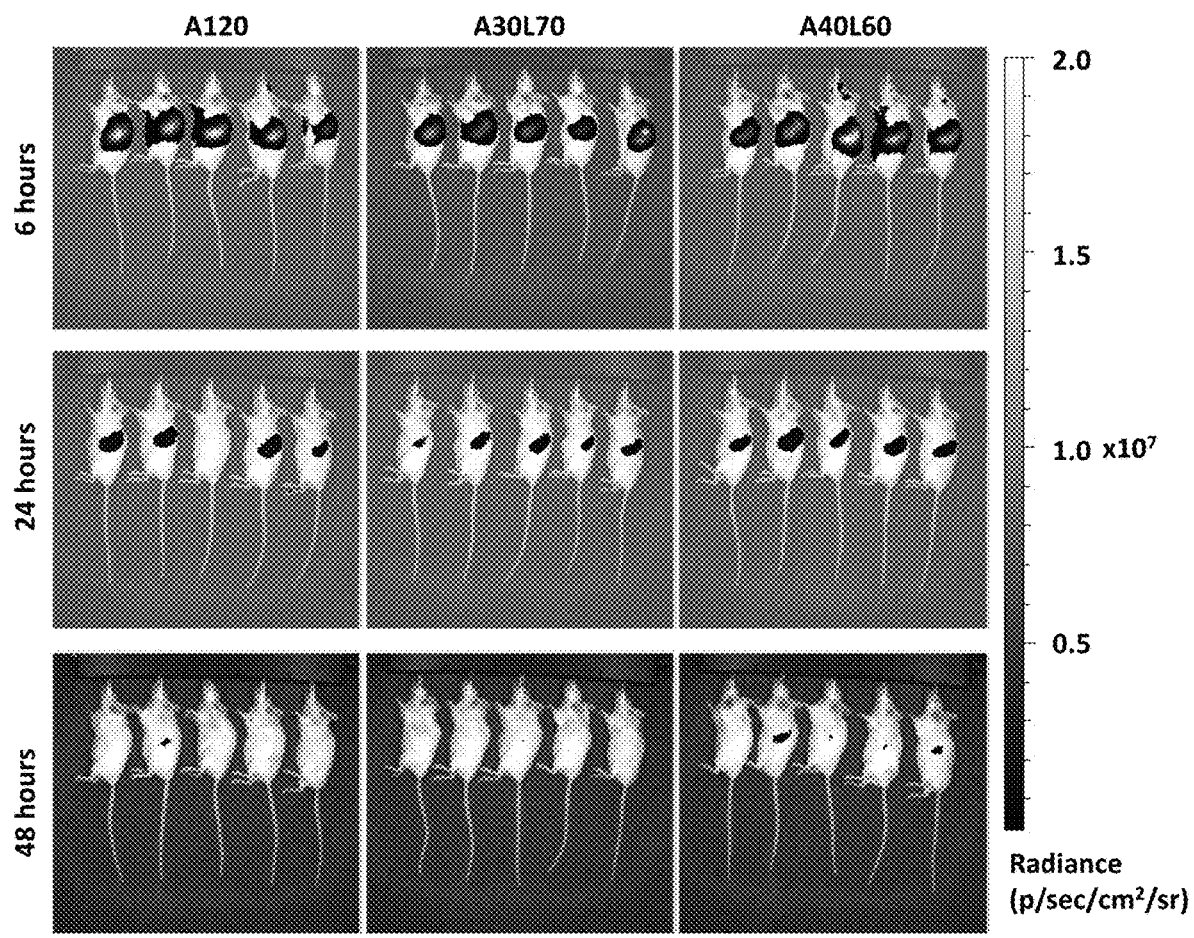
Figure 5B:
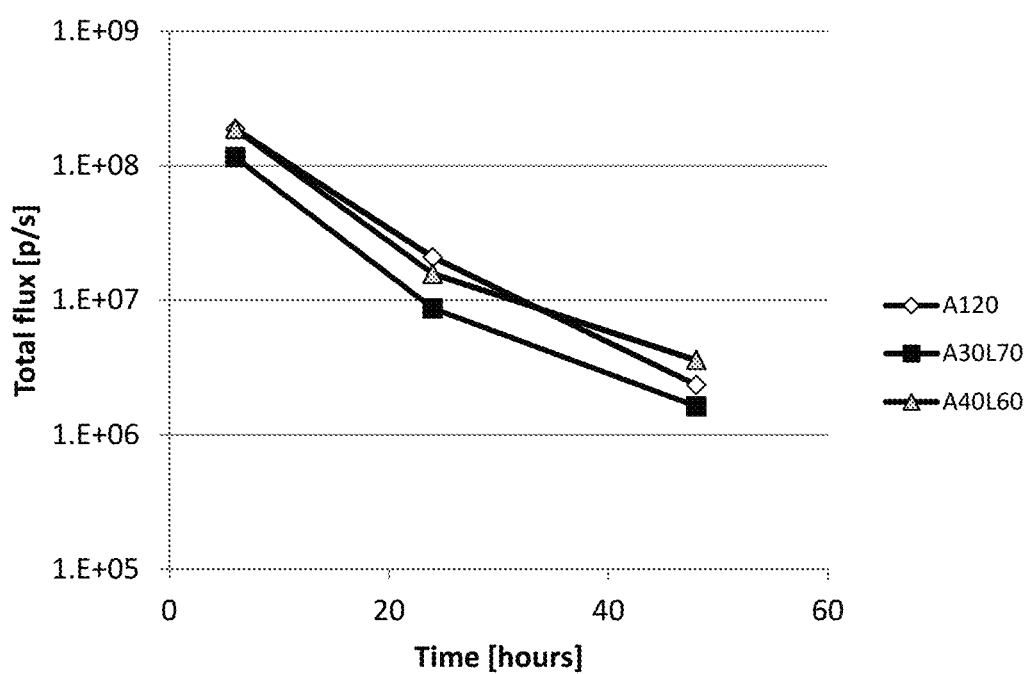

FIGS. 5A-5B: Functional In Vivo Characterization of Different Poly(A) Tails

BALB/c mice (n=5) were injected intravenously with RNA-lipoplexes containing 20 μg of RNA coding for Luciferase (Luc-RNA) and carrying the different poly(A)-tails A120, A30L70 or A40L60. Uptake and translation of Luc-RNA were evaluated by in vivo bioluminescence imaging using the IVIS Lumina imaging system (Caliper Life Sciences). Briefly, an aqueous solution of D-luciferin (150 mg/kg body weight) (BD Biosciences) was injected i.p. 6 hours after administration of RNA lipoplexes. 5 min thereafter, emitted photons were quantified (integration time of 1 min). In vivo bioluminescence in regions of interest were quantified as average radiance (photons/sec/cm/sr) using IVIS Living Image 4.0 Software. The intensity of transmitted light originating from luciferase expressing cells within the animal was represented as a color-scale image, where blue is the least intense and red the most intense bioluminescence signal. Grayscale reference images of mice were obtained under LED low light illumination. The images were superimposed using the Living Image 4.0 software. The luciferase signal was monitored over 48 h. FIG. 5A) Luciferase activity in the spleen of the mice is shown. FIG. 5B) Quantification of the cumulative luciferase signal monitored over 48 hours.

Figure 6A:
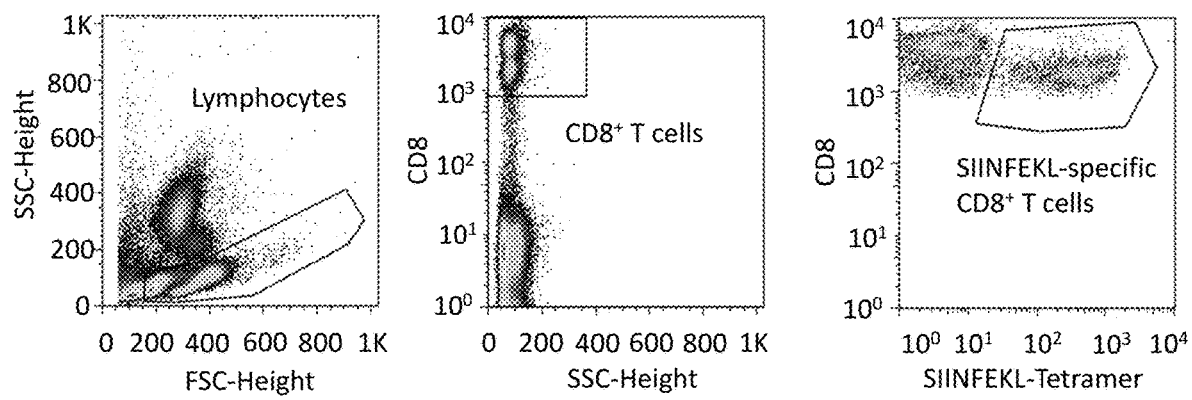
Figure 6B:
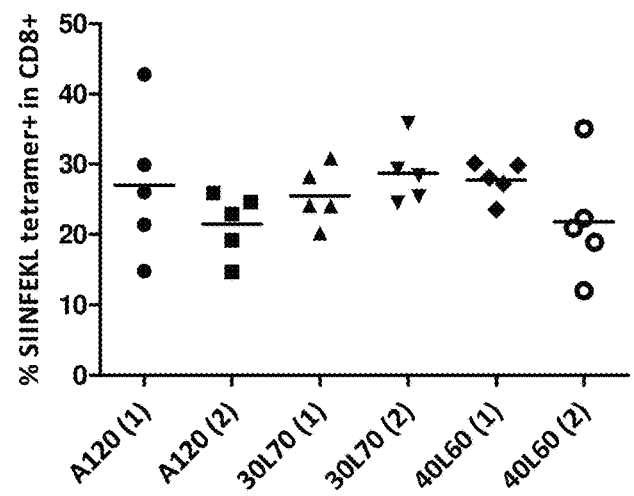

FIGS. 6A-6B: Comparison of Immunological Response of Different Poly(A)-Tails

C57BL/6 mice (n=5) were immunized intravenously in duplicates with RNA-lipoplexes containing 20 μg of RNA coding for the SIINFEKL peptide (SEQ ID NO: 1) carrying the different poly A tails A120, A30L70 or A40L60 on days 0 and 3. The frequencies of antigen specific CD8⁺ T cells were determined in peripheral blood via SIINFEKL-MHC (SEQ ID NO: 1) tetramer staining 5 days after the last immunization (Day 8). Briefly, hypotonicly lysed blood samples were incubated at 4° C. with anti-CD8 antibody (Invitrogen) and H-2 K$^b$/SIINFEKL (SEQ ID NO: 1) tetramer (Beckman-Coulter) and washed to remove unbound antibodies prior to the flow cytometry analysis. Flow cytometric data were acquired on a FACS-Calibur analytical flow cytometer and analyzed by using FlowJo (Tree Star) software. RNA profile was obtained from the 2100 Bioanalyzer of RNA coding for luciferase carrying poly(A)-tails A40L60, A30L70 and A120 respectively. FIG. 6A Gating strategy for antigen-specific CD8⁺ T cells. FIG. 6B Frequencies of antigen-specific CD8⁺ T cells in CD8⁺ T cells.

EXAMPLES

Example 1: Semi-Automated Screen on Poly(dA:dT) Stability

A semi-automated process was established to screen a large number of *E. coli* clones for the integrity of the critical poly(dA:dT) sequence region encoded on the plasmid carried by individual *E. coli* clones. For screening of one specific poly(dA:dT) construct, 96 *E. coli* clones were inoculated and incubated in a 96 well plate at 37° C. Cells were harvested by centrifugation and plasmids were purified on a 96 well plate vacuum-based purification platform. The tested plasmid DNAs contained three SacI restriction sites, cleaving the vector twice in the 3-UTR (3'-untranslated region) and once downstream of the poly(dA:dT) sequence. SacI restriction resulted always in 2 specific bands of 142 bp and 270 bp in size which allowed the calculation of the length of the poly(dA:dT). The third band represented the vector backbone and the antigen with a size depending on the inserted antigen (GOI=gene of interest). An exemplary vector map with the position of the restriction sites and the lengths of the fragments is depicted in FIG. 1B.

To monitor a large number of clones, samples of the SacI restriction digest were applied on a semi-automated capillary electrophoresis system and band patterns between 25 bp and 500 bp were analyzed in high resolution (FIG. 1A shows an example of a restriction analysis of 8 clones). The bands of the internal size standard at 25 bp and 500 bp are marked with black asterisks (*). The bands which represent an intact poly(dA:dT) at 142 bp and 270 bp are marked with black arrows (→). Clone 1 and clone 4 show a subpopulation with a shortened poly(dA:dT) region which results in an additional band between 142 bp and 270 bp (marked with red asterisks (*)). Instability of the poly(dA:dT) is given as the ratio of clones with shortened poly(dA:dT) sequence to clones with an intact poly(dA:dT) sequence.

Example 2: Stability Testing of Different Poly(dA:dT) Constructs

As a model antigen the SIINFEKL peptide (SEQ ID NO: 1) was chosen because in previous experiments the poly(dA:dT) instability of this antigen was reproducibly determined between 50-60% and provides therefore a large experimental window for stability testing. 10 different poly(dA:dT) constructs were designed and fused directly behind the SIINFEKL peptide (SEQ ID NO: 1). A 10 nucleotide linker (L) was inserted in the poly(dA:dT) stretch in different positions of the poly(dA:dT) sequence. The linker sequence (GCATATGACT (SEQ ID NO: 2)) was chosen in a way to contain a balanced contribution of all 4 nucleotides (2×G, 2×C, 3×T and 3×A). 4 constructs were designed with the linker in the middle of the poly(dA:dT) starting with 45 adenosine residues (45×A) on each side (A45L45) with a step-wise increase of 5×A both sides ending with 60×A on each side of the linker (A50L50, A55L55 and A60L60, respectively). The 6 remaining constructs contained like A50L50 100×A in total. However, the linker was inserted after 20×A, followed by the linker sequence and another 80×A (A20L80). Accordingly, the linker was inserted after 30×A (A30L70), 40×A (A40L60), 60×A (A60L40), 70×A (A70L30) and 80×A (A80L20) respectively. 96 clones of each of the 10 constructs were analyzed for poly(dA:dT) integrity with the described restriction analysis method. All 10 linker containing constructs showed a beneficial effect on poly(dA:dT) stability compared to the A120 (see FIG. 2). The determined stability data is summarized in Table 1. Construct A45L45 showed a more than 6-fold higher stability compared to the control A120, however, the step-wise increase of the total length of the poly(dA:dT) led to a higher instability as reflected by only 1.66-fold remaining stabilization of A60L60. Stabilization of constructs with 100×A and the linker sequence at varying positions of the poly(dA:

dT) sequence ranged from 2.9-fold for A20L80 to 13-fold for A40L60. Surprisingly, A30L70 and A40L60 showed a particular high stabilization of the poly(dA:dT) region. Taken together, our results demonstrate that the insertion of a 10 nucleotide random sequence has a stabilizing effect on the poly(dA:dT) integrity. Especially the region between position 30 and position 50 of the poly(dA:dT) region is particular sensitive to poly(dA:dT) shortening. Introduction of linker sequences in this sequence area led to a further increases of the poly(dA:dT) stability by at least 2-fold as compared to the other constructs (see Table 1 and FIG. 2).

TABLE 1

Summary of Poly (dA:dT) stability testing. Depicted is the percentage of clones with shortened poly (dA:dT) sequence and the resulting stabilization of the poly (dA:dT) sequence compared to the polyA120.

| Poly(dA:dT) construct | Cleavage [% of tested clones] | Stablization [fold of A120] |
|---|---|---|
| A120 | 55.9 | 1 |
| A45L45 | 8.8 | 6.4 |
| A50L50 | 10.7 | 5.2 |
| A55L55 | 21.1 | 2.7 |
| A60L60 | 33.7 | 1.7 |
| A60L40 | 8.9 | 6.3 |
| A70L30 | 13.8 | 4.0 |
| A80L20 | 13.6 | 4.1 |
| A40L60 | 4.3 | 13.0 |
| A30L70 | 4.4 | 12.7 |
| A20L80 | 19.3 | 2.9 |

Example 3: Stability of Poly(dA:dT) Constructs in Different E. Coli Strains

In further experiments the specificity and functionality of the superior stability of the constructs A30L70 and A40L60 was tested. The possibility that the observed results of the stability testing are restricted to the tested E. coli strain TOP10 was evaluated by including two other E. coli strains in the testing. Testing for A30L70 and A40L60 was repeated with DH5α, XL1-blue and TOP10 as control respectively. These strains were chosen as i) having a high genetic diversity (see Table 2) and ii) representing E. coli strains which are widely used in molecular biology laboratories.

Instability of the A120 was measured for DH5α at 42% and for XL1-blue at 61.8% and was therefore considered to be comparable to the instability detected for E. coli TOP10 strain (see FIG. 3). Both, A30L70 and A40L60 showed an instability between 3-4%, only for A40L60 in TOP10 instability was slightly elevated to 6.8%. Testing 3 different laboratory strains of E. coli confirmed the results on poly (dA:dT) stabilization. The introduction of a 10 nucleotide linker sequence in the cleavage sensitive region at position 30-50 was identified as a general principle for the genetic stabilization of poly(dA:dT) sequences in different E. coli strains.

TABLE 2

Genotypes of the tested E. coli strains

| Strain | Genotype |
|---|---|
| TOP10 | F-, mcrA, Δ(mrr-hsdRMS-mcrBC), φ80lacZΔM15, ΔlacX74, nupG, recA1, araD139, Δ(ara-leu) 7697, galK galU rpsL (Str$^R$), endA1, λ- |
| DH5α | F-, endA1, glnV44, thi-1, recA1, relA1, gyrA96, deoR, nupG, Φ80, lacZΔM15, Δ (lacZYA-argF) U169, hsdR17 ($r_K^-$ $m_K^+$), λ- |
| XL1-blue | endA1, gyrA96 (nal$^R$), thi-1, recA1, relA1, lac, glnV44, F' [::Tn10, proAB$^+$, lacI$^q$, Δ (lacZ) M15], hsdR17 ($r_K^-$ $m_K^+$) |

Example 4: Functional In Vitro Characterization of Different Poly(A)-Tails

Luciferase reporter-based experiments were performed to elucidate the impact of the identified stabilized poly(A)-tails A30L70 and A40L60 on the functionality of the RNA molecules. The constructs A30L70, A40L60 and A120 were fused to a firefly luciferase reporter gene and the respective messenger RNA was generated by in vitro transcription. The RNA molecules showed comparable integrity and were used for cell electroporation (see Table 3). RNAs were electroporated into human immature dendritic cells, isolated from human bloods which represent the target cells for the company's mRNA tumor vaccine approach. Luciferase translation was monitored over a period of 72 hours. The 3 different mRNA molecules were equally expressed with only minor differences (FIG. 4A). To prove that the functionality of mRNAs in general is not influenced by the nature of the poly(A)-tails, the experiment was repeated in a human fibroblast cell line (CCD cells) and a murine myoblast cell line (C2C12) (FIGS. 4B and 4C). Although a cell type-specific pattern of the mRNA translation was monitored over the time neither human nor murine cell lines showed differences in protein expression by mRNAs containing different poly(A)-tails.

TABLE 3

Integrity of luciferase encoding IVT RNAs

| RNA | Integrity [%] |
|---|---|
| hAg-Kozak-Luciferase-2hBgUTR-A40L60 | 79 |
| hAg-Kozak-Luciferase-2hBgUTR-A30L70 | 81 |
| hAg-Kozak-Luciferase-2hBgUTR-A120 | 83 |

These results demonstrate that the chosen poly(A)-tails have only minor impact on total mRNA functionality in vitro. Therefore linker sequence insertions into the poly(dA: dT) region at position 30 and position 40, respectively, allow a substantial genetic stabilization by maintaining full functionality of the respective RNA molecules.

Example 5: Functional In Vivo Characterization of Different Poly(A)-Tails

For the systemic in vivo application of mRNA for vaccination, RNA lipoplexes are generated by formulation of the RNA together with lipids and administered intravenously. The RNA lipoplexes are meant to target the spleen and to be taken up by immature dendritic cells which translate the respective mRNA. It was aimed to test the two stabilized poly(A)-tails, i.e. A30L70 and A40L60 in a mouse experiment to ensure functional protein expression in vivo. RNA with A120 served as an expression control. Three groups of BALB/c mice with 5 animals each were injected intravenously with RNA-lipoplexes containing firefly luciferase encoding RNAs which had been used for the functional in vitro testing (Table 3) with the different poly(A)-tails (A30L70, A40L60 and A120). Firefly luciferase expression was monitored over 48 hours using an in vivo bioluminescence imaging system (FIG. 5A). The quantification of the cumulative luciferase signals is shown in FIG. 5B. Neither location nor the intensity of the luciferase signal differed significantly between the RNAs with different poly(A)-tails proofing that both stabilized poly(A)-tails are suitable for systemic in vivo applications.

Example 6: Immunological Response to Different Poly(A)-Tails

In a last set of experiments it was assessed if the stabilized poly(A)-tails, A30L70 and A40L60 have an influence on the specific immune response induced by the mRNA vaccine. The stabilized poly(A)-tails and the control A120 were therefore fused to the SIINFEKL peptide (SEQ ID NO: 1) as for the stability testing before. The 3 RNAs containing the poly(A)-tails A30L70, A40L60 and A120 were generated by in vitro transcription and showed comparable quality and integrity (Table 4). 3 groups of C57/BL6 mice, two times 5 animals each, were injected intravenously in duplicates on day 0 and day 3 with RNA lipoplexes containing the different SIINFEKL (SEQ ID NO: 1) RNAs. The RNA-induced immune response was analyzed by determining the frequency of antigen-specific CD8$^+$ T cells 5 days after the last immunization (day 8) by SIINFEKL-MHC (SEQ ID NO: 1) tetramer staining. The respective gating strategy by FACS analysis is depicted in FIG. 6A. The comparison of antigen-specific CD8$^+$ T cell frequencies showed that the RNAs with all tested poly(A)-tails induced an immune response. Thereby no significant differences were detected neither within the same group (2×5 animals for each RNA) nor between the 3 groups which received the different IVT RNAs demonstrating that the stabilized poly(A)-tails did not influence the specific immune response induced by the mRNA (FIG. 6B).

TABLE 4

Integrity of SIINFEKL (SEQ ID NO: 1) enconding IVT RNAs

| IVT RNA | Integrity [%] |
|---|---|
| hAg-Kozak-sec-SIINFEKL(SEQ ID NO: 1)-MITD-2hBgUTR-A40L60 | 82 |
| hAg-Kozak-sec-SIINFEKL(SEQ ID NO: 1)-MITD-2hBgUTR-A30L70 | 81 |
| hAg-Kozak-sec-SIINFEKL(SEQ ID NO: 1)-MITD-2hBgUTR-A120 | 83 |

By establishing a restriction-based analysis method we can show here that the poly(dA:dT) region coding for the poly(A)-tail of an mRNA is genetically instable in common E. coli strains. This instability leads to labor-intensive screening efforts in order to obtain clones with a stable poly(dA:dT) sequence. We demonstrated that the insertion of a 10 nucleotide linker sequence stabilizes this sequence stretch. Thereby position 30 to 50 have been identified as being in especially sensitive to poly(dA:dT) shortening. Linker insertions in this particular region increased the stability further by at least factor 2 compared to insertions at other positions. Stability testing was confirmed in several commonly used E. coli strains. The sequence insertions did not alter the functionality of the respective in vitro transcribed RNAs as demonstrated in several cell lines and by comparison of in vivo activity in mice. Last, the RNA-induced immune response was not influenced by the modification of the poly(A)-tail. Taken together, we identified a tool to stabilize the poly(dA:dT) region genetically which facilitates handling with the respective plasmid DNA and thereby neither influencing the RNA in vitro and in vivo functionality nor the induction of an RNA-specific immune response.

The invention claimed is:

1. A nucleic acid molecule comprising in the 5'→3' direction of transcription:
   (a) a promoter;
   (b) a transcribable nucleic acid sequence or a nucleic acid sequence for introducing a transcribable nucleic acid sequence; and
   (c) a nucleic acid sequence which, when transcribed under the control of the promoter (a), codes for a modified polyadenyl sequence of at least 80 consecutive nucleotides, wherein the modified polyadenyl sequence comprises:
      a linker sequence comprising at least one T, C, or G nucleotide;
      a first sequence of at least 20 A consecutive nucleotides, which is 5' of the linker sequence; and
      a second sequence of at least 20 A consecutive nucleotides, which is 3' of the linker sequence.

2. The nucleic acid molecule as claimed in claim 1, wherein the linker sequence is a sequence of 2 or more consecutive nucleotides, wherein the first and the last nucleotide of said sequence of 2 or more consecutive nucleotides is a nucleotide selected from the group consisting of T, C, and G.

3. The nucleic acid molecule as claimed in claim 1, wherein the modified polyadenyl sequence of at least 80 consecutive nucleotides comprises at least 90 nucleotides.

4. The nucleic acid molecule as claimed in claim 1, wherein the linker sequence is located within a region from position 21 to position 80 of said modified polyadenyl sequence.

5. The nucleic acid molecule as claimed in claim 2, wherein the linker sequence has a length of at least 3 nucleotides.

6. The nucleic acid molecule as claimed in claim 2, wherein said sequence of 2 or more consecutive nucleotides comprises 3 or fewer consecutive A nucleotides.

7. The nucleic acid molecule as claimed in claim 1, wherein the nucleic acid sequences (b) and (c) under the control of the promoter (a) can be transcribed to give a common transcript.

8. The nucleic acid molecule as claimed in claim 1, wherein the modified polyadenyl sequence of at least 80 consecutive nucleotides is located at the 3' end of a transcript.

9. The nucleic acid molecule as claimed in claim 1, which is a closed circular molecule or a linear molecule.

10. The nucleic acid molecule as claimed in claim 1, comprising the transcribable nucleic acid sequence, which comprises a nucleic acid sequence coding for a peptide or protein.

11. The nucleic acid molecule as claimed in claim 1, further comprising one or more members selected from the group consisting of: (i) a reporter gene; (ii) a selectable marker; and (iii) an origin of replication.

12. The nucleic acid molecule as claimed in claim 1, which is suitable, after linearization, for in vitro transcription of mRNA.

13. A method of propagating a nucleic acid molecule, comprising:
   (i) providing a nucleic acid molecule as claimed in claim 1, and
   (ii) propagating said nucleic acid molecule in *Escherichia coli*.

14. The method of claim 13, wherein propagating said nucleic acid molecule in *Escherichia coli* comprises transforming *Escherichia coli* with said nucleic acid molecule and cultivating said transformed *Escherichia coli*.

15. The method of claim 13, which further comprises isolating said nucleic acid molecule from *Escherichia coli* following propagation.

16. A method of obtaining RNA, comprising:
   (i) propagating a nucleic acid molecule according to the method of claim 13, and
   (ii) transcribing in vitro the nucleic acid molecule as a template into RNA.

17. A method of obtaining a peptide or protein, comprising:
   (i) obtaining mRNA encoding a peptide or protein according to the method of claim 16, and
   (ii) translating the mRNA into the peptide or protein sequence.

18. The method as claimed in claim 16, further comprising, prior to (ii), cleaving the nucleic acid molecule.

19. The nucleic acid molecule as claimed in claim 1, comprising the nucleic acid sequence for introducing a transcribable nucleic acid sequence, which comprises a multiple cloning site.

* * * * *